(12) United States Patent
Benner

(10) Patent No.: US 11,426,419 B2
(45) Date of Patent: Aug. 30, 2022

(54) COMPOSITIONS AND METHODS FOR THE REPAIR OF MYELIN

(71) Applicant: Duke University, Durham, NC (US)

(72) Inventor: Eric J. Benner, Durham, NC (US)

(73) Assignee: Duke University, Durham, NC (US)

(*) Notice: Subject to any disclaimer, the term of this patent is extended or adjusted under 35 U.S.C. 154(b) by 86 days.

(21) Appl. No.: 16/910,706

(22) Filed: Jun. 24, 2020

(65) Prior Publication Data
US 2021/0161916 A1 Jun. 3, 2021

Related U.S. Application Data

(63) Continuation of application No. 16/265,438, filed on Feb. 1, 2019, now abandoned, which is a continuation of application No. 15/325,039, filed as application No. PCT/US2015/039770 on Jul. 9, 2015, now Pat. No. 10,238,664.

(60) Provisional application No. 62/022,261, filed on Jul. 9, 2014.

(51) Int. Cl.
*A61K 31/575* (2006.01)
*A61K 35/20* (2006.01)
*C12N 5/079* (2010.01)

(52) U.S. Cl.
CPC ............ *A61K 31/575* (2013.01); *A61K 35/20* (2013.01); *C12N 5/0622* (2013.01); *C12N 2500/36* (2013.01); *C12N 2506/08* (2013.01)

(58) Field of Classification Search
None
See application file for complete search history.

(56) References Cited

U.S. PATENT DOCUMENTS

| | | | |
|---|---|---|---|
| 4,743,597 | A | 5/1988 | Javitt et al. |
| 5,310,742 | A | 5/1994 | Elias |
| RE37,999 | E | 2/2003 | Tipton et al. |
| 7,339,065 | B2 | 3/2008 | Avery et al. |
| 8,165,819 | B2 | 4/2012 | Clermont et al. |
| 8,604,011 | B2 | 12/2013 | Mellon |
| 9,532,968 | B1 | 1/2017 | Nguyen |
| 9,746,481 | B2 | 8/2017 | Everett et al. |
| 10,238,664 | B2 | 3/2019 | Benner |
| 2002/0010128 | A1 | 1/2002 | Parks et al. |
| 2005/0019765 | A1 | 1/2005 | Wellington et al. |
| 2006/0009433 | A1 | 1/2006 | Yao et al. |
| 2006/0035873 | A1 | 2/2006 | Niesor et al. |
| 2007/0093470 | A1 | 4/2007 | Chao et al. |
| 2008/0269183 | A1* | 10/2008 | Mellon ............... A61K 31/57 514/182 |
| 2010/0286053 | A1 | 11/2010 | Kuan et al. |
| 2014/0179656 | A1 | 6/2014 | Kuang et al. |
| 2014/0308687 | A1 | 10/2014 | Keller et al. |
| 2016/0031930 | A1* | 2/2016 | Martinez Botella .... A61P 25/04 514/182 |
| 2017/0007739 | A1 | 1/2017 | Reves et al. |
| 2017/0196892 | A1 | 7/2017 | Benner |

FOREIGN PATENT DOCUMENTS

| | | |
|---|---|---|
| WO | WO 2002/011708 A2 | 2/2002 |
| WO | WO 2008/071960 A2 | 6/2008 |
| WO | WO 2011/103175 A2 | 8/2011 |
| WO | WO 2013/040441 A1 | 3/2013 |
| WO | WO 2013/154752 A1 | 10/2013 |
| WO | 2016007762 | 1/2016 |
| WO | WO 2016/172658 A2 | 10/2016 |
| WO | WO 2017/007836 A1 | 1/2017 |
| WO | WO 2018/132676 A1 | 7/2018 |

OTHER PUBLICATIONS

Communication Conveying Extended European Search Report for EP Application No. 18738460.7 dated Aug. 4, 2020 (Applicant—Duke University) (12 pages).
United States Patent Office Action for U.S. Appl. No. 16/477,826 dated Sep. 30, 2020 (60 pages).
Frohman EM, et al. (2006) Multiple sclerosis—the plaque and its pathogenesis. N Engl J Med. 354(9):942-955.
Non-Final Office Action dated Jan. 24, 2020 for U.S. Appl. No. 16/265,438, filed Feb. 1, 2019 (Inventor—Benner // Applicant—Duke University) (13 pages).
Article 94(3) EPC Communication for E.P. Application No. 15819122.1 dated Jan. 7, 2020 (Inventor—Benner // Applicant—Duke University) (5 pages).
Alberta, "Sonic Hedgehog Is Required during an Early Phase of Oligodendrocyte Development in Mammalian Brain," Molecular and Cellular Neuroscience, 2001, 18, 434-441.
Ayciriex et al., "Development of a novel method for quantification of sterols and oxysterols by UPLC-ESI-HRMS: application to a neuroinflammation rat model," Anal Bioanal Chem, 2012, 404, 3049-3059.
Back et al., "Maturation-Dependent Vulnerability of Perinatal White Matter in Premature Birth," Stroke, 2007, 38, 724-730.
Bai et al., "Gli1 can rescue the in vivo function of Gli2," Development, 2001, 128, 5161-5172.
Beaino et al., "Predictors of cerebral palsy in very preterm infants: the Epipage prospective population-based cohort study," Dev Med Child Neurol, 2010, 52, e119-25.
Benner et al., "Protective astrogenesis from the SVZ niche after injury is controlled by Notch modulator Thbs4," Nature, 2013, 497, 369-373.
Bigler et al., "Volumetric and Voxel-Based Morphometry Findings in Autism Subjects With and Without Macrocephaly," Dev Neuropsychol, 2010, 35(3): 278-295.

(Continued)

*Primary Examiner* — My-Chau T. Tran
(74) *Attorney, Agent, or Firm* — Polsinelli PC

(57) ABSTRACT

Described are oxysterols, pharmaceutical compositions including the oxysterols, and methods of using the oxysterols and compositions for treating diseases and/or disorders related to myelin injury, such as neonatal brain injury, traumatic brain injury, spinal cord injury, cerebral palsy, seizures, cognitive delay, multiple sclerosis, stroke, autism, leukodystrophy, schizophrenia and bipolar disorder.

12 Claims, 13 Drawing Sheets

(56) References Cited

OTHER PUBLICATIONS

Billiards et al., "Myelin abnormalities without oligodendrocyte loss in periventricular leukomalacia," Brain Pathol, 2008, 18, 153-163.
Bittner et al., "Myelin oligodendrocyte glycoprotein (MOG35-55) induced experimental autoimmune encephalomyelitis (EAE) in C57BU6 mice," J. Vis. Exp., 2014, 86: 51275, 5 pages.
Björkhem et al., "Brain Cholesterol: Long Secret Life Behind a Barrier," Arterioclerosis, Thrombosis and Vascular Biology, 2004, 24(5):806-815.
Björkhem et al., "Oxysterols—Friends, Foes, or Just Fellow Passengers?," Arterioscler Thromb Vasc Biol, 2002, 22:734-742.
Briscoe et al., "The mechanisms of Hedgehog signalling and its roles in development and disease," Nature Publishing Group, 2013, 14, 416-429.
Buser et al., "Arrested preoligodendrocyte maturation contributes to myelination failure in premature infants," Ann Neurol, 2012, 71, 93-109.
C.T.F.A., Cosmetic Ingredient Handbook, 1992, pp. 587-592.
Cao et al., "Transplantation of ciliary neurotrophic factor-expressing adult oligodendrocyte precursor cells promotes remyelination and functional recovery after spinal cord injury," Journal of Neuroscience, 2010, vol. 30, Issue 8, pp. 2989-3001.
Caporaso et al., "Ultra-high-throughput microbial community analysis on the Illumina HiSeq and MiSeq platforms," ISME J, 2012, 6, 1621-1624.
Cartagena et al., "24S-hydroxycholesterol effects on lipid metabolism genes are modeled in traumatic brain injury," 2010, Brain Research, vol. 1319, pp. 1-12. (Year: 2010).
Centers for Disease Control and Prevention (CDC), "Economic costs associated with mental retardation, cerebral palsy, hearing loss, and vision impairment--United States, 2003," MMWR Morb Mortal Wkly Rep, 2004, 53, 57-59.
Chau et al., "Postnatal infection is associated with widespread abnormalities of brain development in premature newborns," Pediatr Res, 2012, 71, 274-279.
Cochary et al., "Presence of the plasma membrane proteolipid (plasmolipin) in myelin," J. Neurochem, 1990, 55, 602-610.
Colver et al., "Cerebral palsy," The Lancet, 2014, 383, 1240-1249.
Corcoran et al., "Oxysterols stimulate Sonic hedgehog signal transduction and proliferation of medulloblastoma cells," Proc Natl Acad Sci USA, 2006, 103, 8408-8413.
Cortez et al., "Maternal milk feedings reduce sepsis, necrotizing enterocolitis and improve outcomes of premature infants," J Perinatol, 2018, 38, 71-74.
Counsell et al., "Diffusion-weighted imaging of the brain in preterm infants with focal and diffuse white matter abnormality," Pediatrics, 2003, 112, 1-7.
Deng et al., "Direct visualization of membrane architecture of myelinating cells in transgenic mice expressing membrane-anchored EGFP," Genesis, 2014, 52, 341-349.
Deoni et al., "Breastfeeding and early white matter development: a cross-sectional study," NeuroImage, 2013, 82, 77-86.
Deoni et al., "White-matter relaxation time and myelin water fraction differences in young adults with autism," Psychological Medicine, 2015, 45, 795-805.
Du et al., "Myelin and Axon Abnormalities in Schizophrenia Measured with Magnetic Resonance Imaging Techniques," Biological Psychiatry, 2013, 74(6), 451-457.
Dwyer et al., "Oxysterols are novel activators of the hedgehog signaling pathway in pluripotent mesenchymal cells," Journal of Biological Chemistry, 2007, 282, 8959-8968.
Egan et al., "Toll-like receptor 4-mediated lymphocyte influx induces neonatal necrotizing enterocolitis," J. Clin. Invest., 2016, 126, 495-508.
Fard et al., "BCAS1 expression defines a population of early myelinating oligodendrocytes in multiple sclerosis lesions," Sci Transl Med, 2017, 9, eaam7816.
Ferent et al., "Sonic Hedgehog signaling is a positive oligodendrocyte regulator during demyelination," J. Neurosci, 2013, 33, 1759-1772.
Fischer et al., "Expression of plasmolipin in oligodendrocytes," J. Neurosci. Res, 1991, 28, 8189.
Frohman et al., "Multiple Sclerosis—the Plaque and Its Pathogenesis," the New England Journal of Medicine, 2006, 354(9):942-955.
Gabbi, C., Warner, M. & Gustafsson, J.-A. Biochemical and Biophysical Research Communications. Biochemical and Biophysical Research Communications, 2014, 647-650.
Gibertoni et al., "Positive Effect of Human Milk Feeding during NICU Hospitalization on 24 Month Neurodevelopment of Very Low Birth Weight Infants: an Italian Cohort Study," PLoS One, 2015, 10, e0116552, 13 pages.
Gill et al., "Sterol regulators of cholesterol homeostasis and beyond: the oxysterol hypothesis revisited and revised," Progress in Lipid Research, 2008, 47(6), pp. 391-404.
Hack et al., "Chronic conditions, functional limitations, and special health care needs of school-aged children born with extremely low-birth-weight in the 1990s," JAMA, 2005, 294, 318-325.
Hermann et al., "Brain development in children with new onset epilepsy: a prospective controlled cohort investigation," Epilepsia, 2010, 51(10), 2038-2046.
Im-Emsap et al., "Disperse Systems," Modern Pharmaceutics, 1979, Chapter 9.
IUPAC, "Rules for the Nomenclature of Organic Chemistry, Section E: Stereochemistry, Recommendations 1974," Pure & Appl. Chem., 1976, vol. 45, pp. 11-30.
Janowski et al., "An oxysterol signalling pathway mediated by the nuclear receptor Lxr alpha," Nature, 1996, 383, 728-731.
Kase et al., "22-Hydroxycholesterols regulate lipid metabolism differently than T0901317 in human myotubes," Biochim Biophys Acta, 2006, 1761, 1515-1522.
Kim et al., "20(S)-Hydroxycholesterol Inhibits PPARy Expression and Adipogenic Differentiation of Bone Marrow Stromal Cells Through a Hedgehog-Dependent Mechanism," Journal of Bone and Mineral Research, 2007, 22, 1711-1719.
Klevay, "Myelin and traumatic brain injury: the copper deficiency hypothesis," Medical Hypotheses 2013, 81(6), 995-998.
Kottke et al., "Tablet Dosage Forms," Modern Pharmaceutics, 1979, Chapter 10.
Kuczynski et al., "Using Qiime to analyze 16S rRNA gene sequences from microbial communities," Curr Protoc Microbiol, 2012, Chapter 1, Unit 10.7, 28 pages.
Lagace et al., "Dynamic contribution of nestin-expressing stem cells to adult neurogenesis," Journal of Neuroscience, 2007, 27, 12623-12629.
Lauth et al., "Inhibition of Gli-mediated transcription and tumor cell growth by small-molecule antagonists," Proc Natl Acad Sci USA, 2007, 104, 8455-8460.
Le Mandat Schultz et al., "Expression of TLR-2, TLR-4, NOD2 and pNF-κB in a Neonatal Rat Model of Necrotizing Enterocolitis," PLoS One, 2007, 2, e1102-9.
Lehmann et al., "Activation of the nuclear receptor Lxr by oxysterols defines a new hormone response pathway," Journal of Biological Chemistry, 1997, 272, 3137-3140.
Leoni et al., "Side chain oxidized oxysterols in cerebrospinal fluid and the integrity of blood-brain and blood-cerebrospinal fluid barriers," Journal of Lipid Research, 2003, 44(4): 793-799.
Lin et al., "The detection of 20(S)-hydroxycholesterol in extracts of rat brains and human placenta by a gas chromatograph/mass spectrometry technique," the Journal of Steroid Biochemistry and Molecular Biology, 2003, 85, 57-61.
Madan et al., "Gut microbial colonisation in premature neonates predicts neonatal sepsis," Archives of Disease in Childhood—Fetal and Neonatal Edition, 2012, 97, F456-62.
Mai et al., "Distortions in development of intestinal microbiota associated with late onset sepsis in preterm infants," PLoS One, 2013, 8, e52876.
Makoukji et al., "Interplay between LXR and Wnt/β-Catenin Signaling in the Negative Regulation of Peripheral Myelin Genes by Oxysterols," The Journal of Neuroscience, 2011, 31(26): 96209629.
Martinez-Biarge et al., "Predicting motor outcome and death in term hypoxic-ischemic encephalopathy," Neurology, 2011, 76, 2055-2061.

(56) References Cited

OTHER PUBLICATIONS

Maxwell, "Damage to Myelin and Oligodendrocytes: a Role in Chronic Outcomes Following Traumatic Brain Injury?," Brain Sci, 2013, 3(3): 1374-1394.
McCutcheon's vol. 1, Emulsifiers & Detergents, 1994, North American Edition, pp. 236-239.
McIntyre et al., "A systematic review of risk factors for cerebral palsy in children born at term in developed countries," Dev Med Child Neurol, 2013, 55, 499-508.
McMurdie et al., "phyloseq: an R package for reproducible interactive analysis and graphics of microbiome census data," PLoS One, 2013, 8, e61217.
Meffre et al., "Liver X receptors alpha and beta promote myelination and remyelination in the cerebellum," Proceedings of the National Academy of Sciences of the United States of America, 2015, vol. 112, No. 24, pp. 7592.
Meffre et al., "Opposite effect of LXR on myelination process in the central and peripheral nervous systems and interplay with Wnt pathways," Endocrine Abstracts, 2012. Retreived from the Internet on Dec. 14, 2017 <http://www.endocrine-abstracts.org/ea/0029/ea0029p487.htm>.
Mercier et al., "Neurodevelopmental outcome of extremely low birth weight infants from the Vermont Oxford network: 1998-2003," Neonatology, 2010, 97, 329-338.
Miller et al., "Experimental autoimmune encephalomyelitis in the mouse," Curr Protoc Immunol, 2007, Unit—15.1, 26 pages.
Mitha et al., "Neonatal Infection and 5-year Neurodevelopmental Outcome of Very Preterm Infants," Pediatrics, 2013, 132, e372—e380.
Nachtergaele et al., "Oxysterols are allosteric activators of the oncoprotein Smoothened," Nature Chemical Biology, 2012, 8, 211-220.
Nedelcu et al., "Oxysterol binding to the extracellular domain of smoothened in Hedgehog signaling," Nature Chemical Biology, 2013, 9, 557-564.
Nobuta et al., "STAT3-mediated astrogliosis protects myelin development in neonatal brain injury," Ann Neurol. 2012, 72(5): 750-765.
Ortega et al., "Sonic hedgehog promotes generation and maintenance of human forebrain Olig2 progenitors," Front Cell Neurosci, 2013, 7, 254.
Pandit et al., "Diffusion magnetic resonance imaging in preterm brain injury," Neuroradiology, 2013, 55, 65-95.
Paredes et al., "Extensive migration of young neurons into the infant human frontal lobe," Science, 2016, 354(6308): aaf7073, 14 pages.
Pataj et al., "Quantification of oxysterols in human plasma and red blood cells by liquid chromatography high-resolution tandem mass spectrometry," Journal of Chromatography A, 2016, 1439, 82-88.
Paulson et al., "Differential abundance analysis for microbial marker-gene surveys," Nat Methods, 2013, 10, 1200-1202.
Przygonski et al., "Determination of cholesterol oxidation products in milk powder and infant formulas by gas chromatography and mass spectrometry," Nahrung, 2000, 44, 122-125.
Ragot et al., "Absence of correlation between oxysterol accumulation in lipid raft microdomains, calcium increase, and apoptosis induction on 158N murine oligodendrocytes," Biochemical Pharmacology, 2013, 86, 67-79.
Remington's Pharmaceutical Sciences, 15th Ed. 1975, pp. 335-337.
Rohatgi et al., "Patched1 Regulates Hedgehog Signaling at the Primary Cilium," Science, 2007, 317, 372-376.
Samanta et al., "Inhibition of Gli1 mobilizes endogenous neural stem cells for remyelination," Nature, 2015, 526(7373): 448-452.
Shah et al., "Adverse Neurodevelopment in Preterm Infants with Postnatal Sepsis or Necrotizing Enterocolitis is Mediated by White Matter Abnormalities on Magnetic Resonance Imaging at Term," The Journal of Pediatrics, 2008, 153, 170-175.e1.
Shankaran et al., "Whole-Body Hypothermia for Neonates with Hypoxic—Ischemic Encephalopathy," N. Engl J Med 2005, 353: 1574-1584.
Sorrells et al., "Human hippocampal neurogenesis drops sharply in children to undetectable levels in adults," Nature, 2018, 555, 377-381.
Svensson et al., "Crystal structure of the heterodimeric complex of LXRα and RXRβ ligand-binding domains in a fully agonistic conformation," EMBO J, 2003, 22, 4625-4633.
Volpe et al., "The developing oligodendrocyte: key cellular target in brain injury in the premature infant," International Journal of Developmental Neuroscience: the Official Journal of the International Society for Developmental Neuroscience, 2011, 29, 423-440.
Volpe, "Brain injury in premature infants: a complex amalgam of destructive and developmental disturbances," the Lancet Neurology, 2009, 8(1): 110-124.
Volpe, "Postnatal Sepsis, Necrotizing Enterocolitis, and the Critical Role of Systemic Inflammation in White Matter Injury in Premature Infants," the Journal of Pediatrics, 2008, 153(2): 160-163.
Wang, "Role of Sonic Hedgehog Signaling in Oligodendrocyte Differentiation," Neurochem Res, 2016, 41, 3289-3299.
Weiner et al., "Plasma 24S-hydroxycholesterol and other oxysterols in acute closed head injury," Brain Inj, 2008, 22(7-8): 611-615.
Woodward et al., "Neonatal MRI to predict neurodevelopmental outcomes in preterm infants," N. Engl J Med, 2006, 355, 685-694.
Woodward et al., "Neonatal White Matter Abnormalities an Important Predictor of Neurocognitive Outcome for Very Preterm Children," PLoS One, 2012, 7, e51879, 9 pages.
Wynn et al., "Defective innate immunity predisposes murine neonates to poor sepsis outcome but is reversed by TLR agonists," Blood, 2008, 112, 1750-1758.
Wynn et al., "Increased mortality and altered immunity in neonatal sepsis produced by generalized peritonitis," Shock, 2007, 28(6): 675-683.
You et al., "Myelin damage of hippocampus and cerebral cortex in rat pentylenetetrazol model," Brain Research, 2011, 1381, 208-216.
Zhou et al., "Longitudinal analysis of the premature infant intestinal microbiome prior to necrotizing enterocolitis: a case-control study," PLoS One, 2015, 10, e0118632.
Zuercher et al., "Discovery of tertiary sulfonamides as potent liver X receptor antagonists," J Med Chem, 2010, 53, 3412-3416.
International Search Report and Written Opinion for Application No. PCT/US2015/039770 dated Oct. 8, 2015 (9 pages).
International Search Report and Written Opinion for Application No. PCT/US2018/013525 dated Apr. 4, 2018 (11 pages).
European Patent Office Extended Search Report for Application No. 15819122.1 dated Jan. 19, 2018 (10 pages).
United States Patent Office Action for U.S. Appl. No. 15/325,039 dated Dec. 21, 2017 (11 pages).
United States Patent Office Notice of Allowance for U.S. Appl. No. 15/325,039 dated Nov. 1, 2018 (5 pages).
European Patent Office Action for Application No. 15819122.1 dated Jan. 7, 2020 (5 pages).
United States Patent Office Action for U.S. Appl. No. 16/265,438 dated Jan. 24, 2020 (14 pages).

* cited by examiner

FIG. 3A
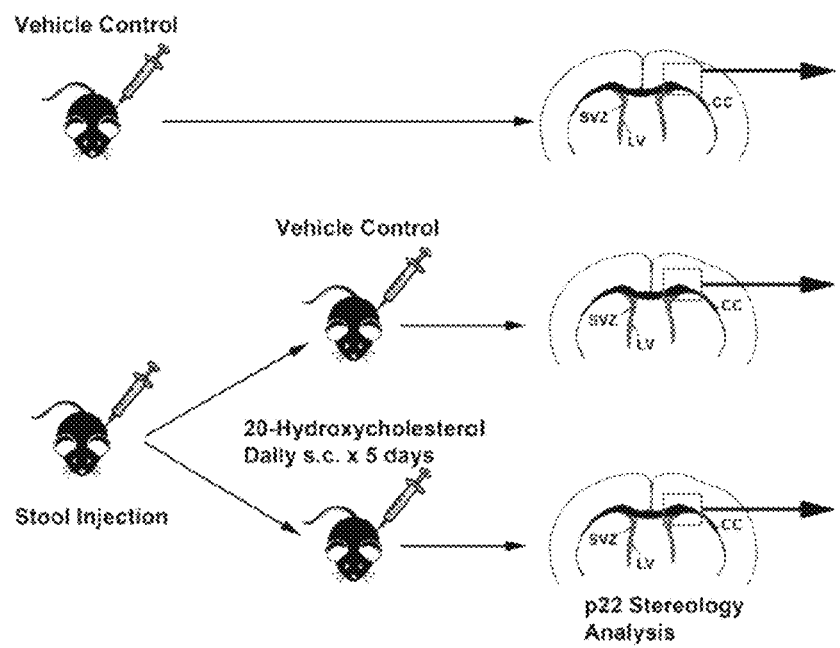
FIG. 3B
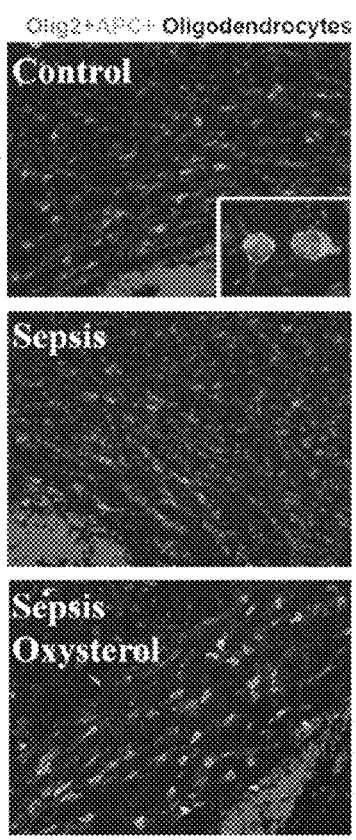
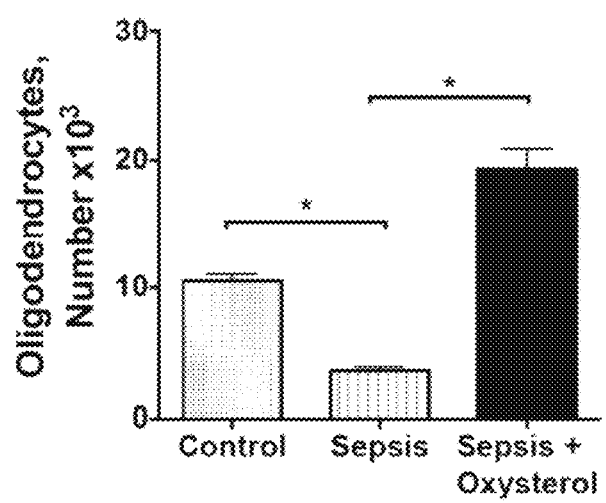
FIG. 3C

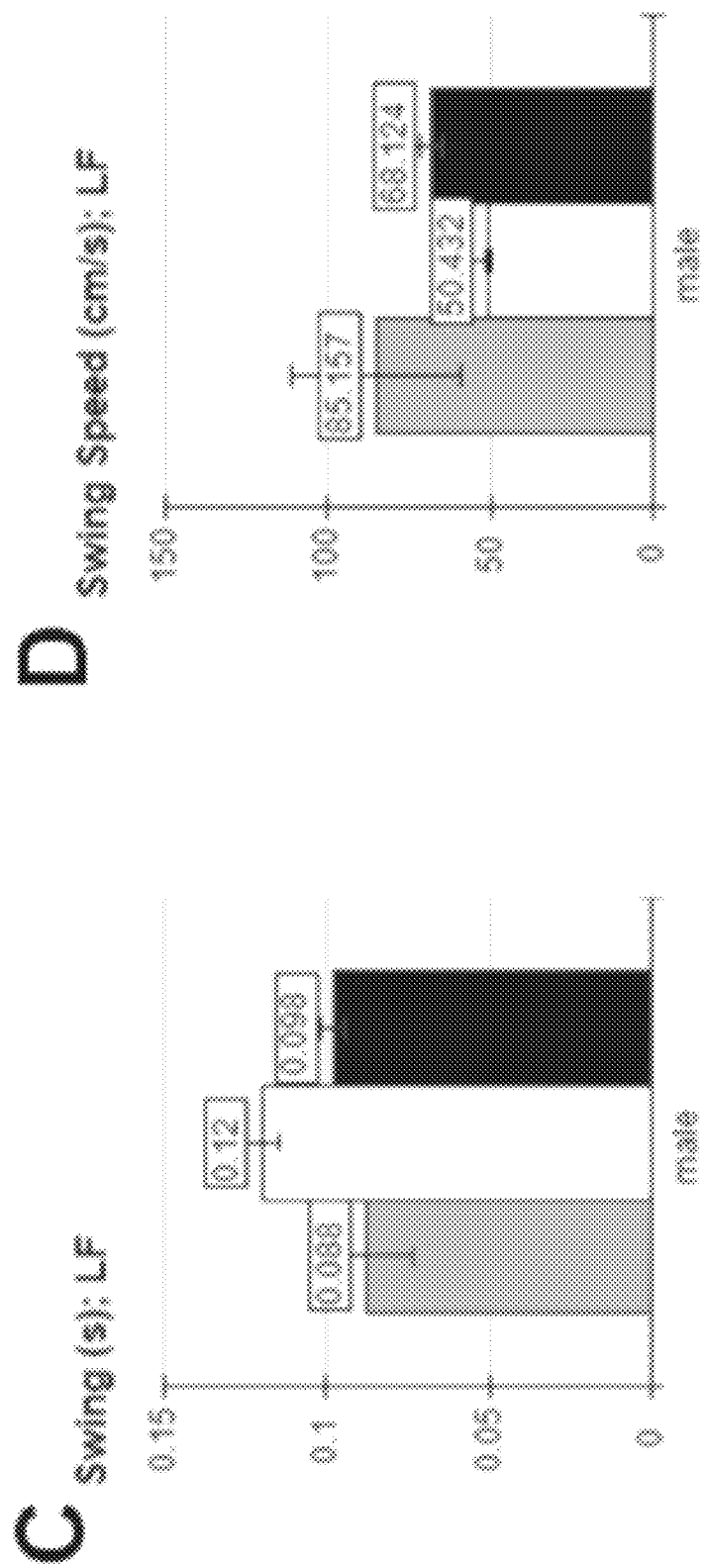

COMPOSITIONS AND METHODS FOR THE REPAIR OF MYELIN

CROSS-REFERENCE TO RELATED APPLICATIONS

This application is a continuation of U.S. patent application Ser. No. 16/265,438, filed Feb. 1, 2019, which is a continuation of U.S. patent application Ser. No. 15/325,039, filed Jan. 9, 2017, which is a U.S. national stage filing under 35 U.S.C. 371 of International Application No. PCT/US2015/039770, filed Jul. 9, 2015, which application claims priority to U.S. Provisional Patent Application No. 62/022,261, filed Jul. 9, 2014, the entire contents of each of which are incorporated are hereby incorporated by reference.

TECHNICAL FIELD

The present disclosure relates to compounds, compositions, and methods for treating diseases and/or disorders related to myelin injury, such as neonatal brain injury, traumatic brain injury, spinal cord injury, cerebral palsy, seizures, cognitive delay, multiple sclerosis, stroke, autism, leukodystrophy, schizophrenia and bipolar disorder.

BACKGROUND

About 10% of infants in the United States are born premature and are at significant risk for brain injuries, which may lead to disorders such as cerebral palsy, seizures, and cognitive delay. Myelin injury is the most common form of brain injury impacting neurodevelopment in premature infants. Currently there are no effective therapies for myelin injuries.

Human breast milk is associated with improved cognitive development. Recent studies have shown that a direct correlation between duration of breast-feeding and the integrity of myelination microstructure exists in humans. However, the mechanisms of breast milk-associated improvements in myelin development are unknown.

Accordingly, there exists a need for effective therapies for brain injuries resulting from damaged myelin. In addition, investigation into the mechanisms of breast milk-associated improvements in myelin development may reveal strategies for therapeutic intervention in injured myelin related diseases and/or disorders in infants.

SUMMARY OF THE INVENTION

In one aspect, disclosed is a method of promoting oligodendrogenesis in a subject in need thereof, the method comprising administering a therapeutically effective amount of at least one oxysterol.

In another aspect, disclosed is a method of repairing injured myelin in a subject in need thereof, the method comprising administering a therapeutically effect amount of an oxysterol.

Also disclosed are pharmaceutical compositions comprising the compounds, and methods of using the pharmaceutical compositions for treatment of diseases and/or disorders related to myelin injury.

BRIEF DESCRIPTION OF THE DRAWINGS

FIG. 3A is a diagram of the experimental design used to test oxysterol therapy in sepsis injured perinatal mice.

FIG. 3B is a panel of confocal images of Olig2+APC+ cells within the corpus callosum of control sepsis, and sepsis+oxysterol treated mice.

FIG. 3C is a graph illustrating the increase in oligodendrocyte formation after treatment of mice having sepsis injury with 20α-hydroxycholesterol in comparison to vehicle treated mice with and without sepsis injury.

FIG. 5A-5D are graphs depicting the results of Stand and Step cycle measurements and swing and swing speed meaurements after treatment of mice having sepsis injury with 20α-hydroxycholesterol in comparison to vehicle treated mice with and without sepsis injury.

DETAILED DESCRIPTION

Figures 1A, 1B:
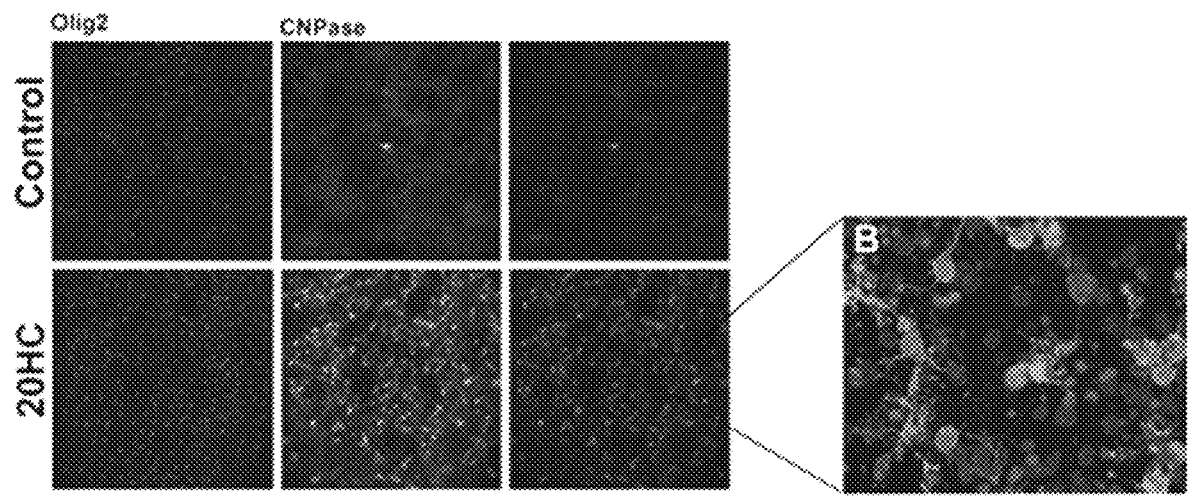
FIG. 1A is a series of confocal micrographs showing differentiated cells stained for oligodendrocyte markers (OLIG2 and CNPase).
FIG. 1B is a magnification of a confocal micrograph of FIG. 1A showing oligodendrocyte morphology.

Disclosed herein are oxysterols useful for the treatment of disorders and diseases related to injury to myelin. The disclosed oxysterols are oxidized derivatives of cholesterol. The disclosed oxysterols can be used to repair injured myelin by promoting oligodendrogenesis from neural stem cells and/or oligodendrocyte precursor cell populations. Injured myelin has been implicated in a number of different diseases and disorders including, but not limited to, neonatal brain injury, traumatic brain injury, spinal cord injury, cerebral palsy, seizures, cognitive delay, multiple sclerosis, stroke, autism, leukodystrophy, schizophrenia and bipolar disorder.

Initially, a perinatal mouse model of myelin injury was developed, which recapitulated the pathological features and motor dysfunction observed in cerebral palsy. Employment of this model led to the discovery of an injury to the cerebral neural stem cell population. Using lineage tracing experiments, it was discovered that these neural stem cells stopped producing oligodendrocytes and began producing astrocytes in response to injury. Spurred by these observations, it was postulated that there may be biological targets within the stem cell population that could redirect these stem cells back into the oligodendrocyte lineage and promote oligodendrocyte differentiation.

For example, the sonic hedgehog (SHH) signaling pathway has been shown to promote oligodendrogenesis in vitro and in vivo. In addition, oxysterols are natural ligands for the SHH pathway and recent studies demonstrated in fibroblast cell culture systems that the oxysterols, 20α-hydroxycholesterol and 22α-hydroxycholesterol, can activate the SHH pathway via direct binding to smoothened (SMO). Once SMO is bound to the oxysterol, it is believed that the negative regulator Patched1 (PTCH1) cannot interact with SMO, resulting in SHH pathway activation and subsequent oligodendrogenesis.

Accordingly, compounds that promote oligodendrogenesis, such as the oxysterols of the present disclosure can be useful in treating diseases related to myelin pathology.

Furthermore, human breast milk may be an appropriate vehicle for the administration of oxysterol therapy to infants in need of such therapy. Multiple naturally occurring oxysterols are identified in human breast milk, increasing the viability of employing its use in therapies for neonatal brain injuries and related disorders and diseases.

In addition, most infants born prematurely are typically administered human breast milk for nourishment. Because oxysterols can be used to promote oligodendrogenesis and healthy myelin, breast milk or infant formula supplemented with additional amounts of oxysterols may be beneficial to promoting brain development in prematurely born infants, regardless of suspected or known brain injury.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The term "oxidized derivative" as used herein, means a compound substituted with an oxygen containing group, such as, but not limited to, at least one of a hydroxyl, oxo, alkoxy, epoxy or carboxy group.

The term "parenterally," as used herein, refers to modes of administration which include intravenous, intramuscular, intraperitoneal, intrasternal, subcutaneous and intraarticular injection and infusion.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

In some instances, the number of carbon atoms in a hydrocarbyl substituent (e.g., alkyl or cycloalkyl) is indicated by the prefix "$C_x$-$C_y$-", wherein x is the minimum and y is the maximum number of carbon atoms in the substituent. Thus, for example, "$C_1$-$C_3$-alkyl" refers to an alkyl substituent containing from 1 to 3 carbon atoms.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. COMPOUNDS

A. Oxysterols

Oxysterols are oxidized derivatives of cholesterol. Oxysterols useful for the methods and compositions of the present disclosure may be oxidized derivatives of cholesterol wherein cholesterol is oxidized at any carbon of cholesterol. Oxysterols useful for the methods and compositions of the present disclosure may be substituted with an oxygen containing group, such as, but not limited to, at least one of a hydroxyl, oxo, alkoxy, epoxy or carboxy group.

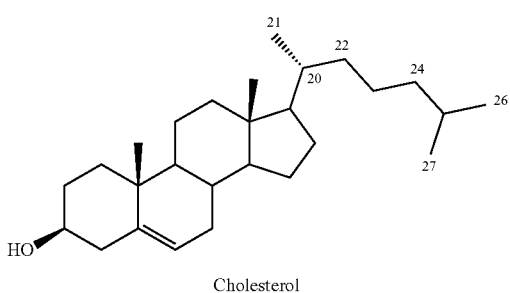 [SMILES: CC(C)CCC[C@@H](C)C1CCC2C3CC=C4C[C@@H](O)CC[C@]4(C)C3CC[C@@]21C]

Cholesterol

Oxysterols may be important in many biological processes, including cholesterol homeostasis, atherosclerosis, sphingolipid metabolism, platelet aggregation, apoptosis, and protein prenylation, though their roles are often poorly understood. Oxysterols are lipophilic and cross the blood brain barrier. They are naturally present in small amounts in the brain and they are known ligands for the Liver X Receptor (LXR) and Sonic Hedgehog (SHH) signaling pathways. Oxysterols may be oxidized at sites on the tetracyclic ring structure or on the C20-27 aliphatic chain. Specific oxysterols include the following:

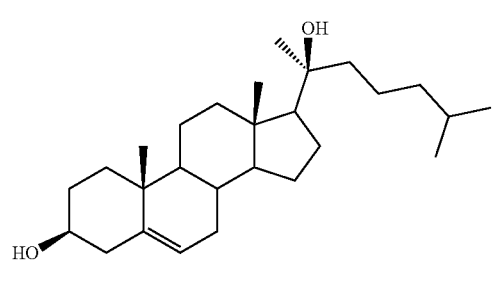

20α-hydroxycholesterol

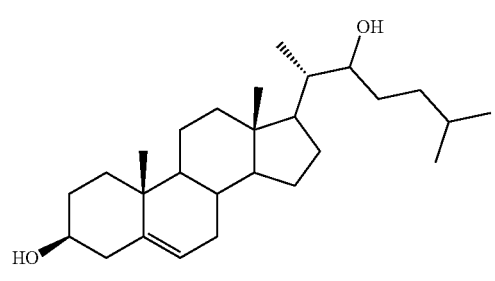

22-hydroxycholesterol

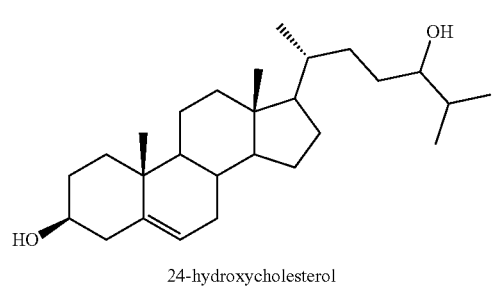

24-hydroxycholesterol

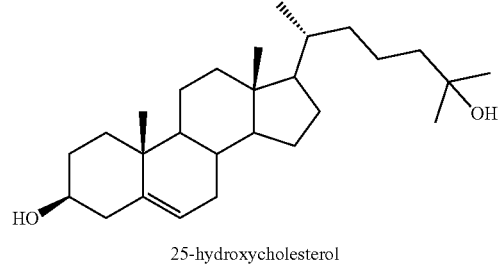

25-hydroxycholesterol

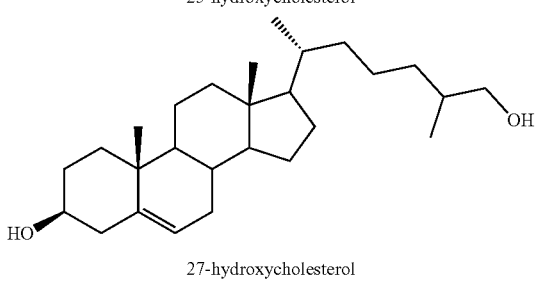

27-hydroxycholesterol

In certain embodiments, the oxysterol may be selected from the group consisting of:
20α-hydroxycholesterol;
22(R)-hydroxycholesterol;
22(S)-hydroxycholesterol;
24(R)-hydroxycholesterol;
24(S)-hydroxycholesterol;
25-hydroxycholesterol; and
27-hydroxycholesterol; or a pharmaceutically acceptable salt thereof The compound may exist as a stereoisomer wherein asymmetric or chiral centers are present. The stereoisomer is "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The disclosure contemplates various stereoisomers and mixtures thereof and these are specifically included within the scope of this invention. Stereoisomers include enantiomers and diastereomers, and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

It should be understood that the compound may possess tautomeric forms, as well as geometric isomers, and that these also constitute an aspect of the invention.

The present disclosure also includes an isotopically-labeled compound, which is identical to the recited oxysterols, but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in the disclosed oxysterols are $^{11}C$, $^{13}N$, $^{15}O$, and $^{18}F$. Isotopically-labeled oxysterols can generally be prepared by conventional techniques known to those skilled in the art or by processes analogous to those described in the accompanying Examples using appropriate isotopically-labeled reagent in place of non-isotopically-labeled reagent.

A. Oligodendrocytes and Oligodendrogenesis

Oxysterols of the present disclosure can promote the differentiation of oligodendrocytes from neural stem cells.

Oligodendrocytes are a type of neuroglia. They function to provide support and insulation to axons in the central nervous system by creating the myelin sheath. Oligodendrocytes arise during development from oligodendrocyte precursor cells. Most oligodendrocytes develop during embryogenesis and early postnatal life from restricted periventricular germinal regions.

Oligodendrocytes are found in the central nervous system (CNS) and originate from the ventral ventricular zone of the embryonic spinal cord. They are the last cell type to be generated in the CNS. Myelination is only prevalent in a few brain regions at birth and continues into adulthood. The entire process is not complete until about 25-30 years of age.

As part of the nervous system, oligodendrocytes are closely related to nerve cells and provide a supporting role for neurons. In addition, the nervous system of mammals depends on myelin sheaths, which reduce ion leakage and decrease the capacitance of the cell membrane. Myelin also increases impulse speed, as saltatory propagation of action potentials occurs at the nodes of Ranvier in between Schwann cells (of the PNS) and oligodendrocytes (of the CNS). Myelinating oligodendrocytes are a part of the white matter and myelination is an important component of intelligence.

1. Biomarkers of Oligodendrogenesis

Oligodendrogenesis may be determined by measuring the concentration of certain biomarkers in tissue. These biomarkers include Oligodendrocyte Transcription Factor (OLIG2), 2',3'-Cyclic-Nucleotide 3'-Phosphodiesterase (CNPase), and Myelin Basic Protein (MBP). The presence of, or an increase in the concentration of these biomarkers may indicate oligodendrocyte formation.

a. Oligodendrocyte Transcription Factor

Oligodendrocyte transcription factor (OLIG2) is a basic helix-loop-helix transcription factor encoded by the Olig2 gene. The protein is of 329 amino acids in length, 32 kDa in size and contains 1 basic helix-loop-helix DNA-binding domain. The expression of OLIG2 is mostly restricted in central nervous system, and is well known for determining oligodendrocyte differentiation.

OLIG2 is mostly expressed in restricted domains of the brain and spinal cord ventricular zone which give rise to oligodendrocytes and specific types of neurons. During embryogenesis, OLIG2 first directs motor neuron fate by establishing a ventral domain of motor neuron progenitors and promoting neuronal differentiation. OLIG2 then switches to promoting the formation of oligodendrocyte precursors and oligodendrocyte differentiation at later stages of development.

b. 2',3'-Cyclic-nucleotide 3'-phosphodiesterase

2',3'-Cyclic-nucleotide 3'-phosphodiesterase (CNPase) is a myelin-associated enzyme that makes up 4% of total CNS myelin protein, and is thought to undergo significant age-associated changes. It is named for its ability to catalyze the phosphodiester hydrolysis of 2',3'-cyclic nucleotides to 2'-nucleotides, though a cohesive understanding of its specific physiologic functions are still ambiguous.

CNPase is expressed exclusively by oligodendrocytes in the CNS, and the appearance of CNPase seems to be one of the earliest events of oligodendrocyte differentiation. CNPase may play a critical role in the events leading up to myelination.

c. Myelin Basic Protein

Myelin basic protein (MBP) is important in the process of myelination of nerves in the nervous system. The myelin sheath is a multi-layered membrane, unique to the nervous system, that functions as an insulator to greatly increase the velocity of axonal impulse conduction. MBP maintains the correct structure of myelin, interacting with the lipids in the myelin membrane.

The disclosed oxysterols can promote the formation of oligodendrocytes such that a treated subject has an increase of oligodendrocyte formation. The increase in oligodendrocyte formation may be measured relative to oligodendrocyte levels pretreatment in the subject. The increase of oligodendrocyte formation may be measured relative to oligodendrocyte levels in an untreated subject. The increase in oligodendrocyte formation may be measured relative to oligodendrocyte levels in an untreated control.

The disclosed oxysterols may promote an increase in oligodendrocyte formation of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, at least 160%, at least 170%, at least 180%, at least 190%, at least 200%, at least 250%, at least 300%, at least 450%, or at least 500%.

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, thrichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

B. General Synthesis

The disclosed oxysterols may be prepared by synthetic processes or by metabolic processes. Preparation of the compounds by metabolic processes includes those occurring in the human or animal body (in vivo) or processes occurring in vitro.

The compounds and intermediates may be synthesiszed, isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

A disclosed compound may have at least one basic atom or functional group whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, hydroxybutyric, camphorsulfonic, malic, phenylacetic, aspartic, or glutamic acid, and the like.

Optimum reaction conditions and reaction times for each individual step can vary depending on the particular reactants employed and substituents present in the reactants used. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in P G M Wuts and T W Greene, in Greene's book titled Protective Groups in Organic Synthesis ($4^{th}$ ed.), John Wiley & Sons, NY (2006), which is incorporated herein by reference in its entirety. Synthesis of the compounds of the invention can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material, or by resolution of a mixture of the geometric isomers of the compound or intermediates using a standard procedure such as chromatographic separation.

3. PHARMACEUTICAL COMPOSITIONS

The disclosed compounds may be incorporated into pharmaceutical compositions suitable for administration to a subject (such as a patient, which may be a human or non-human).

The pharmaceutical compositions may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of a compound of the disclosure [e.g., an oxysterol] are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of a compound of a disclosed oxysterol may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The pharmaceutical compositions may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Thus, the compounds and their physiologically acceptable salts and solvates may be formulated for administration by, for example, solid dosing, eyedrop, in a topical oil-based formulation, injection, inhalation (either through the mouth or the nose), implants, or oral, buccal, parenteral, or rectal administration. Techniques and formulations may generally be found in "Remington's Pharmaceutical Sciences", (Meade Publishing Co., Easton, Pa.). Therapeutic compositions must typically be sterile and stable under the conditions of manufacture and storage.

The route by which the disclosed compounds are administered and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

Carriers for systemic administration typically include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition is typically about 50 to about 90%.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of lubricant(s) in a systemic or topical composition is typically about 5 to about 10%.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition is typically about 5 to about 50%.

Suitable disintegrants include agar, alginic acid and the sodium salt thereof, effervescent mixtures, croscarmelose, crospovidone, sodium carboxymethyl starch, sodium starch glycolate, clays, and ion exchange resins. The amount of disintegrant(s) in a systemic or topical composition is typically about 0.1 to about 10%.

Suitable colorants include a colorant such as an FD&C dye. When used, the amount of colorant in a systemic or topical composition is typically about 0.005 to about 0.1%.

Suitable flavors include menthol, peppermint, and fruit flavors. The amount of flavor(s), when used, in a systemic or topical composition is typically about 0.1 to about 1.0%.

Suitable sweeteners include aspartame and saccharin. The amount of sweetener(s) in a systemic or topical composition is typically about 0.001 to about 1%.

Suitable antioxidants include butylated hydroxyanisole ("BHA"), butylated hydroxytoluene ("BHT"), and vitamin E. The amount of antioxidant(s) in a systemic or topical composition is typically about 0.1 to about 5%.

Suitable preservatives include benzalkonium chloride, methyl paraben and sodium benzoate. The amount of preservative(s) in a systemic or topical composition is typically about 0.01 to about 5%.

Suitable glidants include silicon dioxide. The amount of glidant(s) in a systemic or topical composition is typically about 1 to about 5%.

Suitable solvents include water, isotonic saline, ethyl oleate, glycerine, hydroxylated castor oils, alcohols such as ethanol, and phosphate buffer solutions. The amount of solvent(s) in a systemic or topical composition is typically from about 0 to about 100%.

Suitable suspending agents include AVICEL RC-591 (from FMC Corporation of Philadelphia, Pa.) and sodium alginate. The amount of suspending agent(s) in a systemic or topical composition is typically about 1 to about 8%.

Suitable surfactants include lecithin, Polysorbate 80, and sodium lauryl sulfate, and the TWEENS from Atlas Powder Company of Wilmington, Del. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition is typically about 0.1% to about 5%.

Although the amounts of components in the systemic compositions may vary depending on the type of systemic composition prepared, in general, systemic compositions include 0.01% to 50% of active [e.g., an oxysterol] and 50% to 99.99% of one or more carriers. Compositions for parenteral administration typically include 0.1% to 10% of actives and 90% to 99.9% of a carrier including a diluent and a solvent.

Compositions for oral administration can have various dosage forms. For example, solid forms include tablets, capsules, granules, and bulk powders. These oral dosage forms include a safe and effective amount, usually at least about 5%, and more particularly from about 25% to about 50% of actives. The oral dosage compositions include about 50% to about 95% of carriers, and more particularly, from about 50% to about 75%.

Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic acid and croscarmelose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof.

Capsules (including implants, time release and sustained release formulations) typically include an active compound (e.g., an oxysterol), and a carrier including one or more diluents disclosed above in a capsule comprising gelatin. Granules typically comprise a disclosed compound, and preferably glidants such as silicon dioxide to improve flow characteristics. Implants can be of the biodegradable or the non-biodegradable type.

The selection of ingredients in the carrier for oral compositions depends on secondary considerations like taste, cost, and shelf stability, which are not critical for the purposes of this invention.

Solid compositions may be coated by conventional methods, typically with pH or time-dependent coatings, such that a disclosed compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT coatings (available from Rohm & Haas G.M.B.H. of Darmstadt, Germany), waxes and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid compositions, which may be administered orally, may include a disclosed oxysterol compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the subject compounds include sublingual, buccal and nasal dosage forms. Such compositions typically include one or more of soluble filler substances such as diluents including sucrose, sorbitol and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

The disclosed compounds can be topically administered. Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions include: a disclosed compound (e.g., an oxysterol), and a carrier. The carrier of the topical composition preferably aids penetration of the compounds into the skin. The carrier may further include one or more optional components.

The amount of the carrier employed in conjunction with a disclosed compound is sufficient to provide a practical quantity of composition for administration per unit dose of the medicament. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

A carrier may include a single ingredient or a combination of two or more ingredients. In the topical compositions, the carrier includes a topical carrier. Suitable topical carriers include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of a topical composition may further include one or more ingredients selected from emollients, propellants, solvents, humectants, thickeners, powders, fragrances, pigments, and preservatives, all of which are optional.

Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition is typically about 5% to about 95%.

Suitable propellants include propane, butane, isobutane, dimethyl ether, carbon dioxide, nitrous oxide, and combinations thereof. The amount of propellant(s) in a topical composition is typically about 0% to about 95%.

Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols. The amount of solvent(s) in a topical composition is typically about 0% to about 95%.

Suitable humectants include glycerin, sorbitol, sodium 2-pyrrolidone-5-carboxylate, soluble collagen, dibutyl phthalate, gelatin, and combinations thereof. Specific humectants include glycerin. The amount of humectant(s) in a topical composition is typically 0% to 95%.

The amount of thickener(s) in a topical composition is typically about 0% to about 95%.

Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. The amount of powder(s) in a topical composition is typically 0% to 95%.

The amount of fragrance in a topical composition is typically about 0% to about 0.5%, particularly, about 0.001% to about 0.1%.

Suitable pH adjusting additives include HCl or NaOH in amounts sufficient to adjust the pH of a topical pharmaceutical composition.

In an embodiment, the pharmaceutical composition may include human breast milk. The active pharmaceutical ingredient may be a component of human breast milk. The human breast milk may thus be administered to a subject in need of the active pharmaceutical ingredient.

In another embodiment, some infants may not be able to take food or medication by mouth. For example, infants with acute brain injury are critically ill and may not be able to take food or medication by mouth. Accordingly, total parenteral nutrition (TPN) may be administered through a central line. TPN contains the hydration and nutrients needed to sustain life and grow the infant. Calories are delivered via carbohydrates, protein, and lipids. The lipids may be administered as an intralipid emulsion. Oxysterol therapy may be added to the intralipid emulsion for intravenous administration, for example, through a central line. An example of a commercially available intralipid emulsion is a 20% fat emulsion containing soybean oil, egg yolk, phospholipids, and glycerin. Intralipid emulsions are commercially available.

4. METHODS OF TREATMENT

The disclosed oxysterols and compositions may be used in methods for treatment of disorders and diseases related to brain injury, in particular, injury to myelin. The methods of treatment may comprise administering to a subject in need of such treatment a composition comprising a therapeutically effective amount of an oxysterol. These methods promote the formation of oligodendrocytes, cells which function to provide support and insulation to axons in the central nervous system by creating the myelin sheath. Thus, the formation of oligodendrocytes may serve to create myelin and repair damaged myelin in subjects with injured myelin.

The compositions may be useful for treating and preventing certain diseases and disorders in humans and animals related to myelin injury. Treatment or prevention of such diseases and disorders can be effected by promoting oligodendrogenesis in a subject, by administering a compound or composition of the disclosure, either alone or in combination with another active agent as part of a therapeutic regimen to a subject in need thereof.

Diseases and/or disorders which may be treated and/or prevented by the disclosed methods include neonatal brain injury, traumatic brain injury, spinal cord injury, cerebral palsy, seizures, cognitive delay, multiple sclerosis, stroke, autism, leukodystrophy, schizophrenia and bipolar disorder. The neonatal brain injury may include at least one of diffuse white matter injury, periventricular leukomalacia (PVL), hypoxic-ischemic encephalopathy (HIE), neonatal stroke, and grade 3-4 intraventricular hemorrhages (IVH).

a. Neonatal Brain Injury

In humans, myelin development begins prenatally and continues into young adulthood to achieve complex neurological functions. Failure of proper myelin development is a common pathology in neonatal brain injury associated with preterm and term births associated with hypoxic-ischemia or other insults. The pathology, collectively called neonatal white matter injury (WMI), ranges from diffuse non-necrotic changes affecting mainly subcortical white mater (hypoxic-ischemic encephalitis, HIE) to focal lesions affecting periventricular white matter (periventricular leukomalacia, PVL), and is characterized by underdeveloped myelin. Afflicted children frequently present with diminished cognitive, motor, and psychiatric functions that persist beyond infancy.

b. Traumatic Brain Injury

Nearly two million people suffer traumatic brain injury in the US each year. These injuries adversely alter the metabolism of myelin. Furthermore, the loss of central myelinated nerve fibers continues over the chronic post-traumatic phase after injury (Maxwell, W. *Brain Sci.* 2013, 3(3), 1374-1394.).

c. Spinal Cord Injury

There are an estimated 10,000 to 12,000 spinal cord injuries every year in the U.S. These injuries sever or crush the nerve fibers that run through the spinal cord, potentially leading to complete paralysis and loss of sensation below the level of the injury. A traumatic blow to the spinal cord also typically causes a loss of myelin and the death of oligodendrocytes. Myelin is needed to insulate the electrical signals transmitted by nerve fibers. Further, transplants of oligodendrocyte precursor cells (OPCs) improve recovery in rats with spinal cord, underscoring the importance of remyelination in behavioral improvement after a spinal cord injury.

d. Cerebral Palsy

Cerebral palsy is characterized by damage to myelin sheaths. When axons become unmyelinated, they affect the ability of the brain to transmit signals as efficiently as normal myelinated nerve cells. In turn, poorly transmitted signals translate to an impaired nervous system. However, there are no efficient mechanisms within the human body for repairing myelin sheaths around unmyelinated axons.

e. Seizures

Epilepsy is a chronic neurological disorder characterized by spontaneous recurrent seizures, which also occur in demyelinating diseases of the central nervous system (CNS) with a higher prevalence. Demyelination has been observed in the CNS of epilepsy patients, indicating an association between demyelination and epileptic. A rat model that provides direct evidence that myelin sheath damage in the rat brain started in the early stage of epileptic seizures induction. Furthermore, myelination of axons in children with epilepsy may be slowed by the epileptogenic process or, perhaps, there is seizure-related damage to the posterior corpus callosum myelin sheath surrounding the onset of epilepsy.

f. Multiple Sclerosis

Multiple sclerosis (MS) is characterized by damage to the myelin sheath. The damage is caused by inflammation and the destruction of myelin interferes with nerve conduction. The symptoms of MS relate to this interruption of signaling between neurons. MS is the most common chronic disabling disorder of the central nervous system in young adults. It may be an autoimmune demyelinating disease in which an individual's immune system attacks their own body, in this case the myelin sheath in the brain and spinal cord.

g. Stroke

The myelin sheath can be destroyed by stroke. If the sheath is able to repair and regenerate itself, normal nerve function may return. However, if the sheath is severely damaged, the underlying nerve fiber can die. Because nerve fibers in the CNS rarely regenerate, such damage remains irreversible.

h. Autism

Abnormalities in white matter architecture have been described in human autism. Region-specific decreases in myelin development observed in autism have been suggested to impact brain connectivity. Improving myelination may improve connectivity and mitigate autism-associated symptoms.

i. Leukodystrophy

Leukodystrophy is one of a group of disorders characterized by degeneration of the white matter in the brain. The leukodystrophies are caused by imperfect growth or development of the myelin sheath. When damage occurs to white matter, immune responses can lead to inflammation in the CNS, along with loss of myelin. Leukodystrophy is characterized by specific symptoms including decreased motor function, muscle rigidity, and eventually degeneration of sight and hearing. While the disease is fatal, the age of onset is a key factor as infants are given a lifespan of 2 years, while adults typically live more than a decade after onset.

j. Schizophrenia

There is evidence for abnormalities in both myelin and axons among patients with schizophrenia, when compared with healthy individuals who underwent the same testing. More specifically, there is a reduction in myelination of white matter pathways in schizophrenia. Accordingly, myelination abnormalities in schizophrenia are associated with disturbances in the functional integrity of the white matter.

k. Bipolar Disorder

Oligodendrocyte dysfunction and a loss of white matter have been implicated in bipolar disorder. Imaging studies have shown that patients with bipolar disorder have less white matter than healthy patients. Post-mortem studies have demonstrated a cessation of development of new myelin in early adulthood in patients with bipolar disorder, compared to a steady decrease over a lifetime in healthy patients.

Therefore, it would be beneficial to administer oxysterol therapy to subjects who suffer from neonatal brain injury, traumatic brain injury, spinal cord injury, cerebral palsy, seizures, cognitive delay, multiple sclerosis, stroke, autism spectrum disorders, leukodystrophy, schizophrenia and bipolar disorder.

l. Modes of Administration

Methods of treatment may include any number of modes of administering a disclosed composition. Modes of administration may include tablets, pills, dragees, hard and soft gel capsules, granules, pellets, aqueous, lipid, oily or other solutions, emulsions such as oil-in-water emulsions, liposomes, aqueous or oily suspensions, syrups, elixirs, solid emulsions, solid dispersions or dispersible powders. For the preparation of pharmaceutical compositions for oral administration, the agent may be admixed with commonly known and used adjuvants and excipients such as for example, gum arabic, talcum, starch, sugars (such as, e g, mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. Gelucire®). In the pharmaceutical composition, the agent may also be dispersed in a microparticle, e.g. a nanoparticulate composition.

For parenteral administration, the agent can be dissolved or suspended in a physiologically acceptable diluent, such as, e.g., water, buffer, oils with or without solubilizers, surface-active agents, dispersants or emulsifiers. As oils for example and without limitation, olive oil, peanut oil, cottonseed oil, soybean oil, castor oil and sesame oil may be used. More generally spoken, for parenteral administration, the agent can be in the form of an aqueous, lipid, oily or other kind of solution or suspension or even administered in the form of liposomes or nano-suspensions.

In an embodiment, one or more oxysterol may be administered in a composition comprising human breast milk. The human breast milk may thus be administered orally to a subject in need of oxysterol therapy. The human breast milk may be further supplemented with oxysterols in addition to oxysterols that are naturally present in human breast milk. The oxysterols used for supplementation may be higher doses of one or more oxysterols already present or they may be one or more oxysterols not found to be naturally occurring in human breast milk.

In another embodiment, one or more oxysterol may be administered in a composition comprising infant formula. Infant formula is a manufactured food which purports to be or is represented for special dietary use solely as a food for infants by reason of its simulation of human milk or its suitability as a complete or partial substitute for human milk. The infant formula may thus be administered orally to a subject in need of oxysterol therapy. The infant formula may further comprise at least one oxysterol.

In addition, human breast milk or infant formula comprising at least one oxysterol may be administered to prematurely born infants, regardless of suspected or known brain injury. Because oxysterols can be used to promote oligodendrogenesis and healthy myelin, breast milk or infant formula supplemented with additional amounts of oxysterols may be beneficial to promoting brain development in prematurely born infants.

Infant formula which may be suitable for the methods described herein include, but are not limited to, milk-based formula (for example, SIMILAC®, ENFAMIL®, or GERBER GOOD START®), soy-based formula or lactose-free (for example, SIMILAC SOY ISOMIL®, ENFAMIL PROSOBEE®, GERBER GOOD START SOY®), partially or extensively hydrolyzed formulas (for example, ENFAMIL GENTLEASE®, NUTRAMIGEN®), and formula specially designed for prematurely born infants (for example NEOSURE®, ENFACARE®).

m. Combination Therapies

Additional therapeutic agent(s) may be administered simultaneously or sequentially with the disclosed compounds and compositions. Sequential administration includes administration before or after the disclosed compounds and compositions. In some embodiments, the additional therapeutic agent or agents may be administered in the same composition as the disclosed compounds. In other embodiments, there may be an interval of time between administration of the additional therapeutic agent and the disclosed compounds. In some embodiments, administration of an additional therapeutic agent with a disclosed compound may allow lower doses of the other therapeutic agents and/or administration at less frequent intervals. When used in combination with one or more other active ingredients, the compounds of the present invention and the other active ingredients may be used in lower doses than when each is used singly. Accordingly, the pharmaceutical compositions of the present invention include those that contain one or more other active ingredients, in addition to an oxysterol. The above combinations include combinations of a compound of the present invention not only with one other active compound, but also with two or more other active compounds.

In certain embodiments, the oxysterol can be combined with a variety of neuroprotective strategies. For example, in neonatal brain injury the only approved therapy is whole body hypothermia. This therapy is typically administered within the first 6 hours of birth and is continued for 3 days. The infant is cooled to, for example, 33.5° C. for 72 hours. After 72 hours, the infant is slowly rewarmed to 37° C., for example. Oxysterol therapy could be combined with this whole body hypothermia to mitigate myelin injury and improve neurodevelopmental outcomes.

For the treatment of multiple sclerosis, oxysterols can be combined with standard immunomodulatory therapies including, but not limited to, corticosteroids, beta interferon, glatiramer acetate, dimethyl fumerate, natalizumab, and mitoxantrone.

For the treatment of stroke, oxysterols can be combined with standard approaches to lytic therapy including tissue plasminogen activator (tPA).

For the treatment of schizophrenia, oxysterols can be combined with antipsychotic therapy.

The disclosed compounds may be included in kits comprising the compound (e.g., one or more oxysterols), a systemic or topical composition described above, or both; and information, instructions, or both that use of the kit will provide treatment for medical conditions in mammals (particularly humans). The information and instructions may be in the form of words, pictures, or both, and the like. In addition or in the alternative, the kit may include the medicament, a composition, or both; and information, instructions, or both, regarding methods of application of medicament, or of composition, preferably with the benefit of treating or preventing medical conditions in mammals (e.g., humans).

The compounds and processes of the invention will be better understood by reference to the following examples, which are intended as an illustration of and not a limitation upon the scope of the invention.

n. Evaluation of treatment

Quantification of oligodendrocyte cell numbers in the brain is critical to determining the impact of oxysterol therapy. Stereology is a useful research tool used by neuroscientists to provide accurate and unbiased estimates of cell numbers within specified brain regions. The number of oligodendrocyte numbers is determined using Stereo Investoigator™ software (MBF Bioscience) and a Zeiss AxioImager M2 motorized fluorescent microscope with Apotome structured illumination. Perfusion fixed cryoprotected brains are frozen sectioned at 30 mm and collected free-floating in phosphate buffered saline. Every $4^{th}$ caronal section beginning at the appearance of the lateral ventricles and ending at the level of the anterior commissure are stained for olig2 and APC (CC1). Stained tissue is counter stained with DAPI and mounted on slides. Using Stereo Investigtor, the corpus callosum is outlined under low magnification. Olig2+APC+ nucleated cells are then counted throughout the corpus callosum using a 63× oil objective lens.

The detection of differences in locomotor function is an important tool for the assessment of the severity of many conditions that affect the central nervous system (CNS), peripheral nervous system (PNS) and skeletal structures or muscles. A gait analysis system, such as the CatWalk™ XT, provides automatic and sensitive detection of a full range of parameters related to footprints and the dynamics of gait in animal testing.

Traditionally, methods such as BBB scoring, running wheels, and ink on paper are used. However, these are not always objective and quick to master, nor do they assess the temporal dynamics of gate accurately. The CatWalk XT method is both accurate and objective, and allows for a more detailed assessment of each individual footfall. CatWalk XT has proven itself as an objective, non-intrusive, and accurate tool for researchers in the field of CNS-related disease.

In particular, the regularity index, stand and step cycle, and swing and swing speeds may be measured utilizing these testing methods. Mice which have sustained myelin injury and are administered oxysterol therapy may show an improvement in regularity index, stand and step cycle, and swing and swing speeds over untreated mice. The improvement may be such for each of these measurements that the values determined are similar or the same as that of the values determined for control mice who have sustained no injured myelin.

6. EXAMPLES

20α-Hydroxycholesterol (20HC) and 22α-hydroxycholesterol were purchased commercially from Sigma-Aldrich. All oxysterols were resuspended in DMSO at 12 mM for use in cell culture systems. In vivo studies utilized oxysterols freshly dissolved in corn oil prior to administration.

Example 1. In Vitro Oligodendrocyte Differentiation from Neural Stem Cells

Figures 1C, 1D:
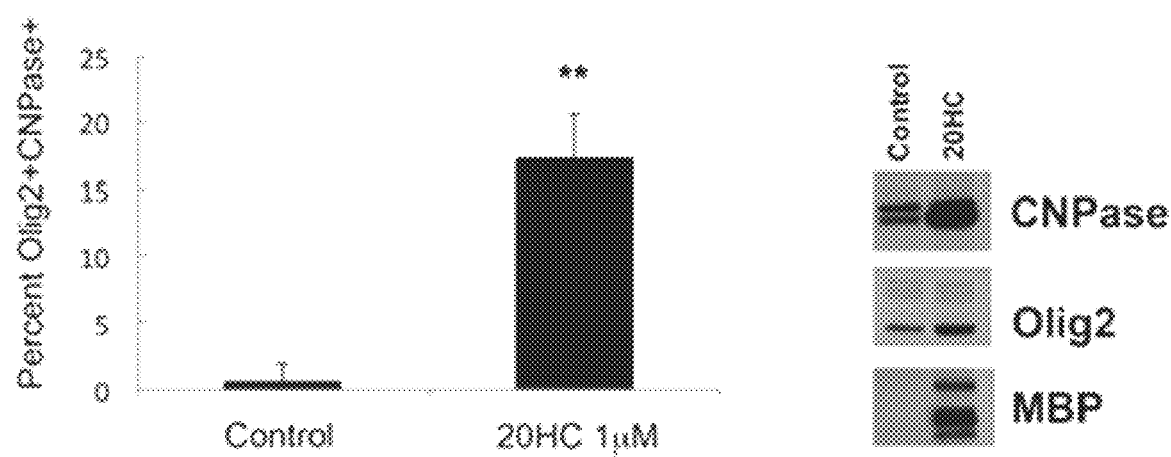
FIG. 1C is a graph illustrating the increase in oligodendrocyte formation after treatment with 20α-hydroxycholesterol.
FIG. 1D is a Western blot analysis showing an increase in oligodendrogenesis biomarkers after treatment with 20α-hydroxycholesterol.

To determine the impact of oxysterol exposure on cellular differentiation, primary neural stem cells from neonatal mice were cultured in chamber slides. Cells were cultured in media alone (control) or 1 μM 20α-hydroxycholesterol for 7 days were then allowed to differentiate for 18 days. The differentiated cells were immunostained for markers of oligodendrocytes (Olig2 and CNPase) and visualized on a confocal microscope (FIG. 1A). Larger magnification of FIG. 1A shows that Olig2+CNPase+ cells have oligodendrocyte morphology (FIG. 1B). Cell counting experiments demonstrated a significant increase in olig2+CNPase+ cells (oligodendrocytes) in the 20α-hydroxycholesterol treated groups (p<0.02; FIG. 1C). Protein samples from control and 20α-hydroxycholesterol treated stem cell cultures were then fractionated and probed for markers of the oligodendrocyte lineage. Western blot analysis revealed an increase in CNPase, Olig2 and myelin basic protein (MBP) in 20α-hydroxycholesterol treated cells (FIG. 1D).

Example 2. In Vivo Oligodendrocyte Differentiation from Neural Stem Cells

Figure 2A:
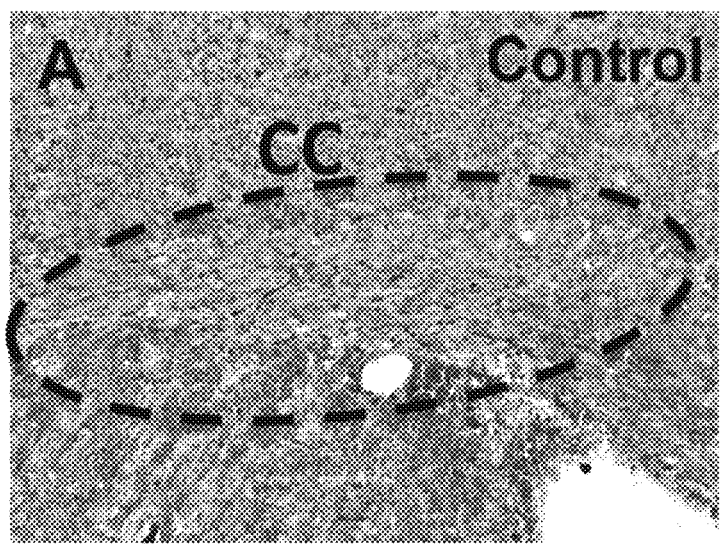
FIG. 2A is a picture of a tissue section of the corpus callosum of a vehicle treated mouse stained for Olig2.
Figure 2B:
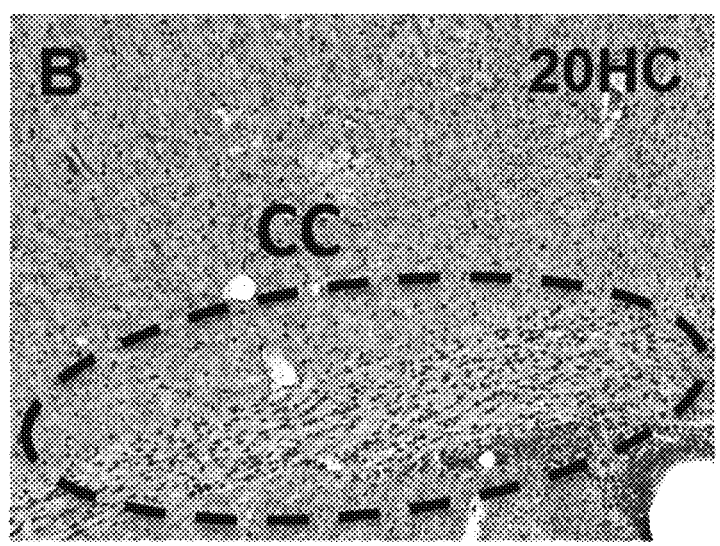
FIG. 2B is a picture of a tissue section of the corpus callosum of a mouse treated with 20α-hydroxycholesterol stained for Olig2.
Figure 2C:
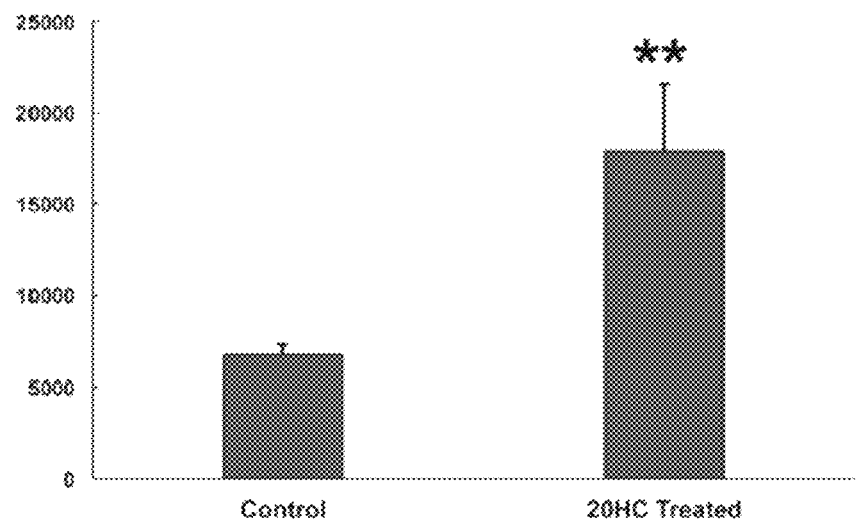
FIG. 2C is a graph illustrating the increase in oligodendrocyte formation after treatment with 20α-hydroxycholesterol.

20α-hydroxycholesterol was administered to uninjured postnatal mice during the normal myelination period to determine if oxysterol exposure increased the numbers of oligodendrocytes in vivo. Five day old mice were administered 4 daily doses of vehicle control (n=4) or 20α-hydroxycholesterol (n=4) subcutaneously (100 mg/kg/day) and rested. Five days after the final injection, the mice were analyzed to quantify the number of olig2+ cells in the corpus callosum (FIG. 2A, 2B). A significant increase in olig2+ cell population was observed in animals receiving 20α-hydroxycholesterol when compared to the control (p<0.02; FIG. 2C).

Taken together, these results show that 20α-hydroxycholesterol demonstrated an ability to significantly promote oligodendrocyte differentiation from neural stem cells both in vitro and in vivo.

Example 3. Perinatal Mouse Model of Myelin Injury

Perinatal bowel perforation is a common complication of premature birth and is strongly linked to myelin injury and cerebral palsy. Using a perinatal mouse model of bowel perforation to induce sepsis-associated diffuse myelin injury on postnatal day 5, sepsis mice were determined to have a 60% reduction of mature oligodendrocytes at postnatal day 25 (FIG. 3).

Example 4. Efficacy of Oxysterol Therapy

To determine the efficacy of oxysterol therapy, the perinatal mouse model was employed to induce injury in mice on postnatal day 5. Commencing 24 hours after injury, mice were administered daily single subcutaneous injections of 20α-hydroxycholesterol (100 mg/kg/day) for 5 days (FIG. 3A). Coronal sections of the brains were analyzed using stereology on postnatal day 25 to determine the number of olig2+APC+ oligodendrocytes in the periventricular white matter of the corpus callosum. Control, sepsis, and sepsis+ oxysterol treated groups were analyzed by immunohistochemistry for olig2 and APC to identify oligodendrocytes (FIG. 3B). Stereological counting revealed a reversal of oligodendrocyte injury in sepsis mice treated with oxysterol (FIG. 3C, p=0.001). Accordingly, treatment with 20α-hydroxycholesterol in sepsis-injured mice significantly increased the amount of oligodendrocytes within the periventricular white matter. In fact, sepsis-injured mice treated with oxysterols had more oligodendrocytes than vehicle treated control mice (FIG. 3B,C).

The impact of oxysterol therapy on motor function in injured mice was also determined. Mice were subjected to sepsis-induced myelin injury on postnatal day 5. Twenty-four hours after injury, septic mice were divided into a vehicle control group and an oxysterol treated group. Treatment with 20α-hydroxycholesterol (100 mg/kg/day) was carried out daily for five days. At two months of age (adult), mice were evaluated on a CatWalk Gait Analysis System (Noldus Inc.). The gait analysis system identified multiple disturbances in the gait of untreated mature mice that survived perinatal sepsis. However, these gait disturbances were not present in mice treated with 20α-hydroxycholesterol.

Figure 4A:
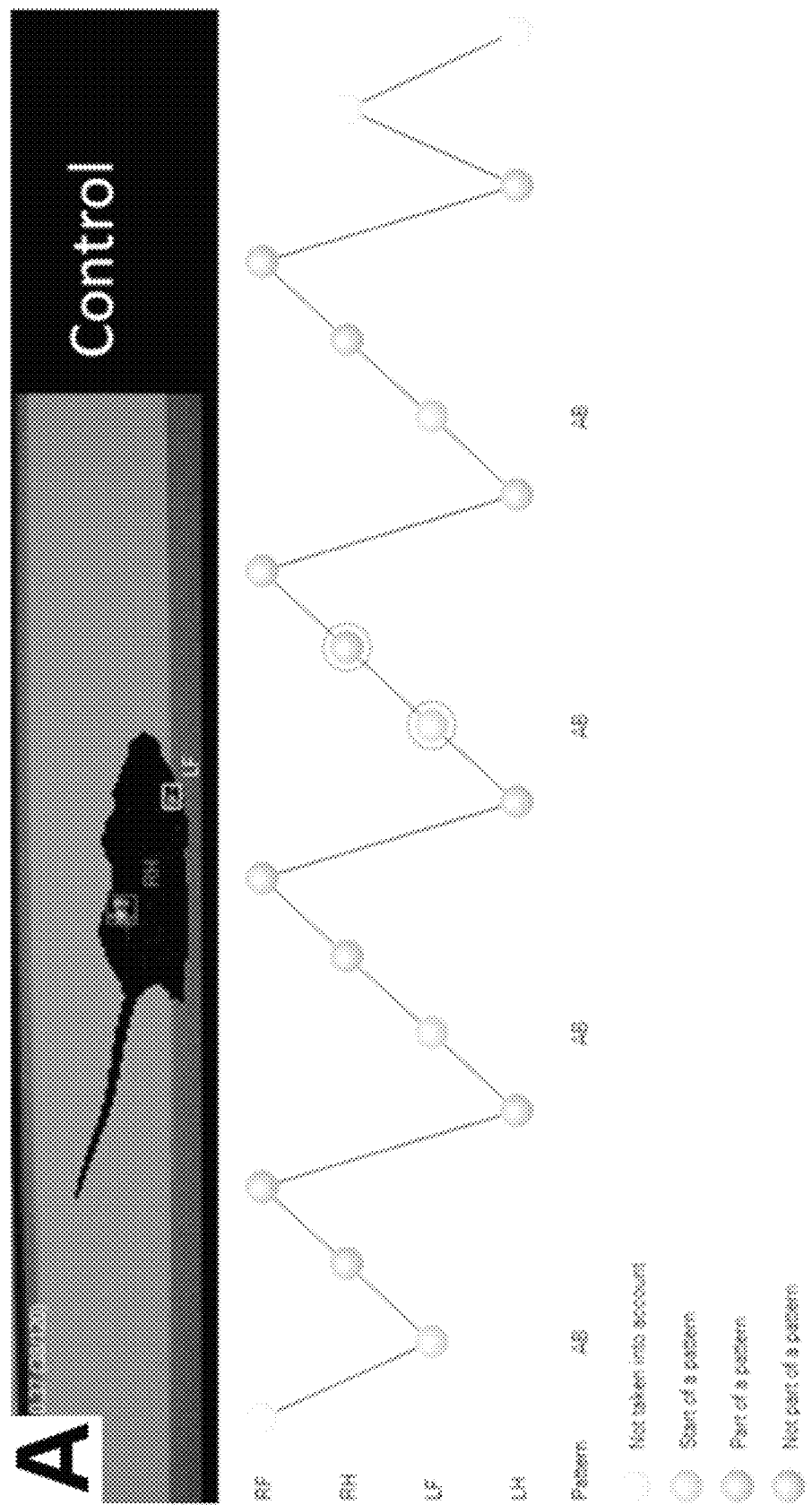
FIGS. 4A-4C are plots of gait measurements after treatment of mice having sepsis injury with 20α-hydroxycholesterol in comparison to vehicle treated mice with and without sepsis injury.
Figure 4B:
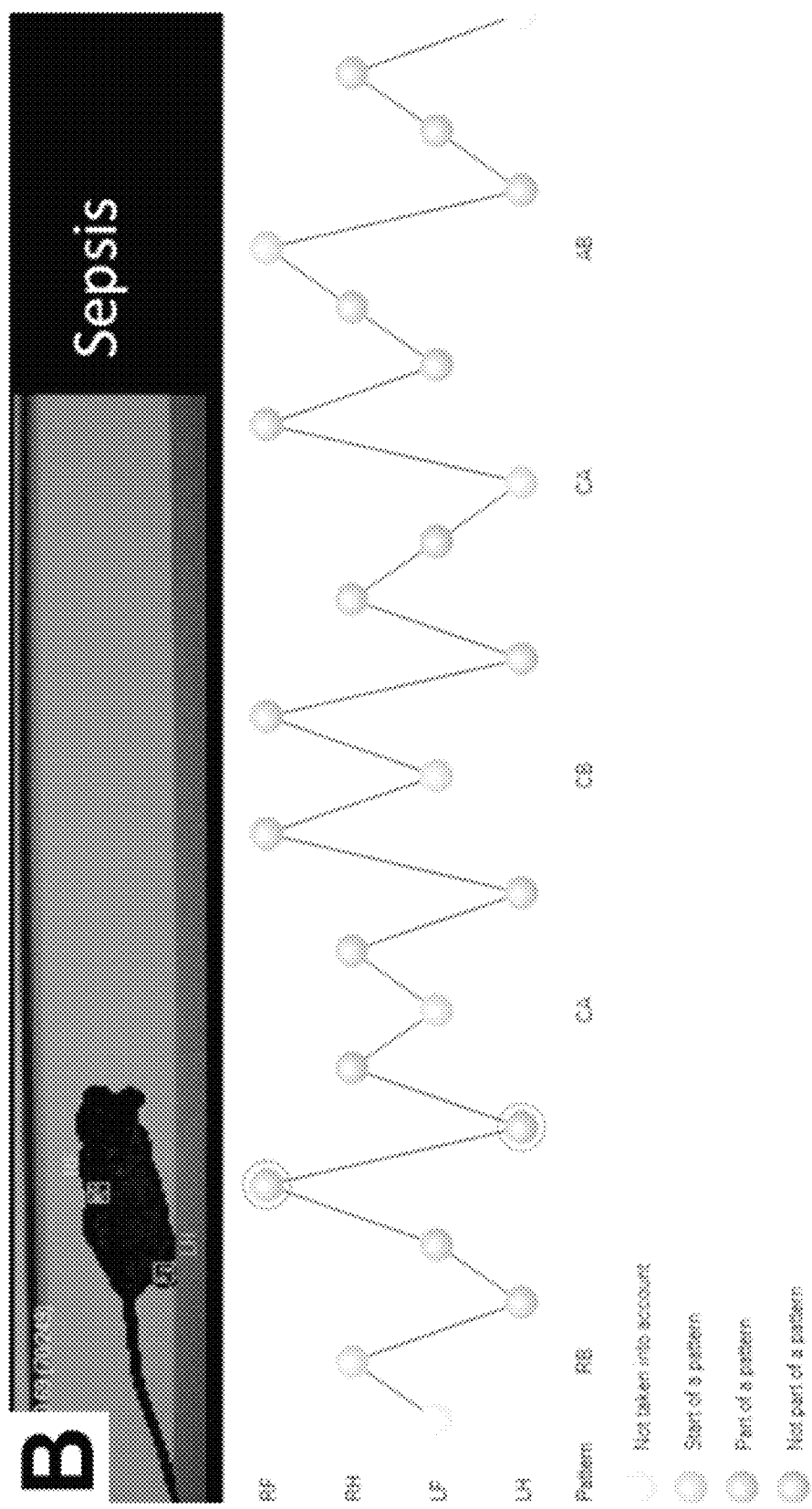
Figure 4C:
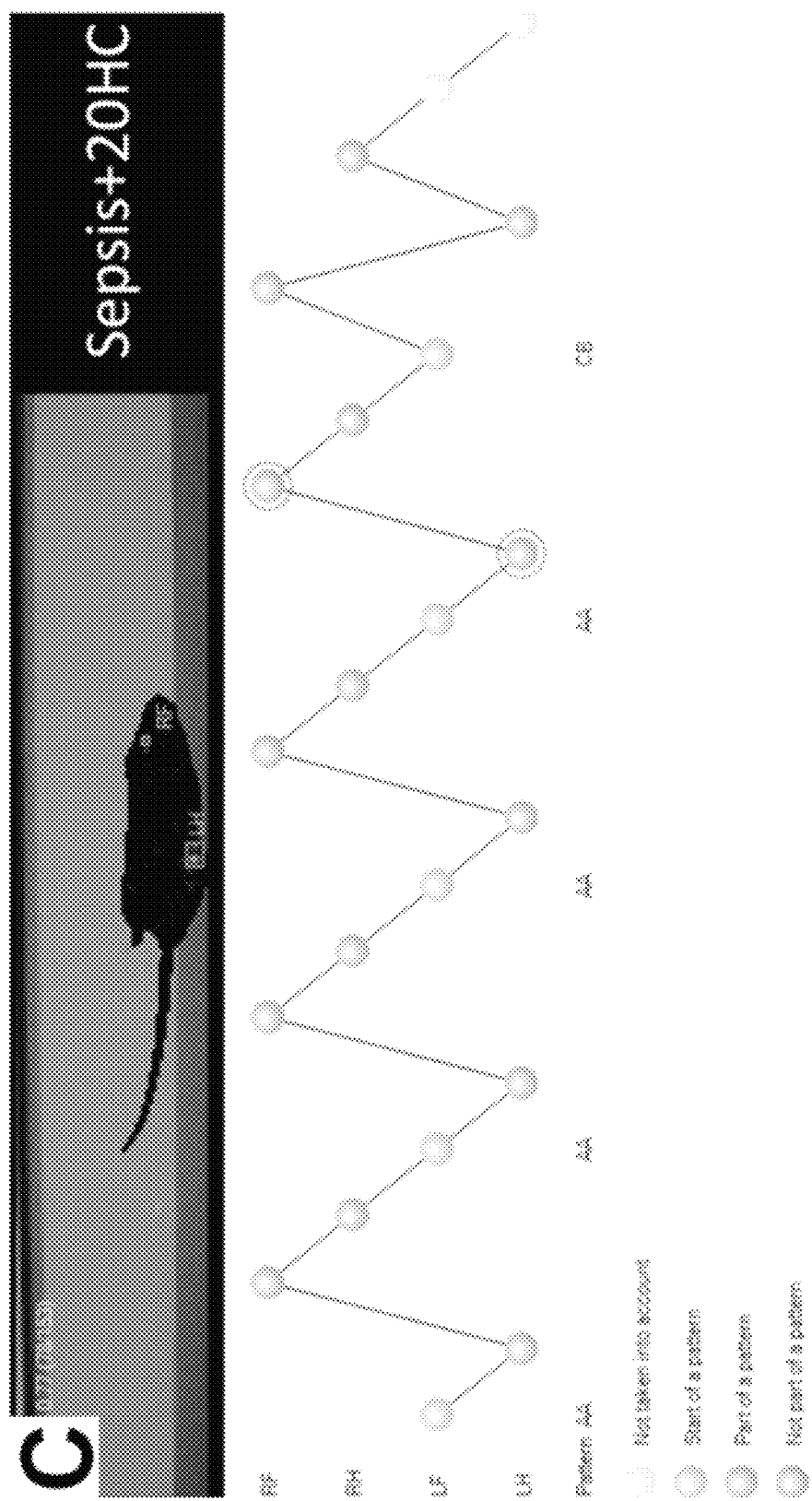
Figure 4D:
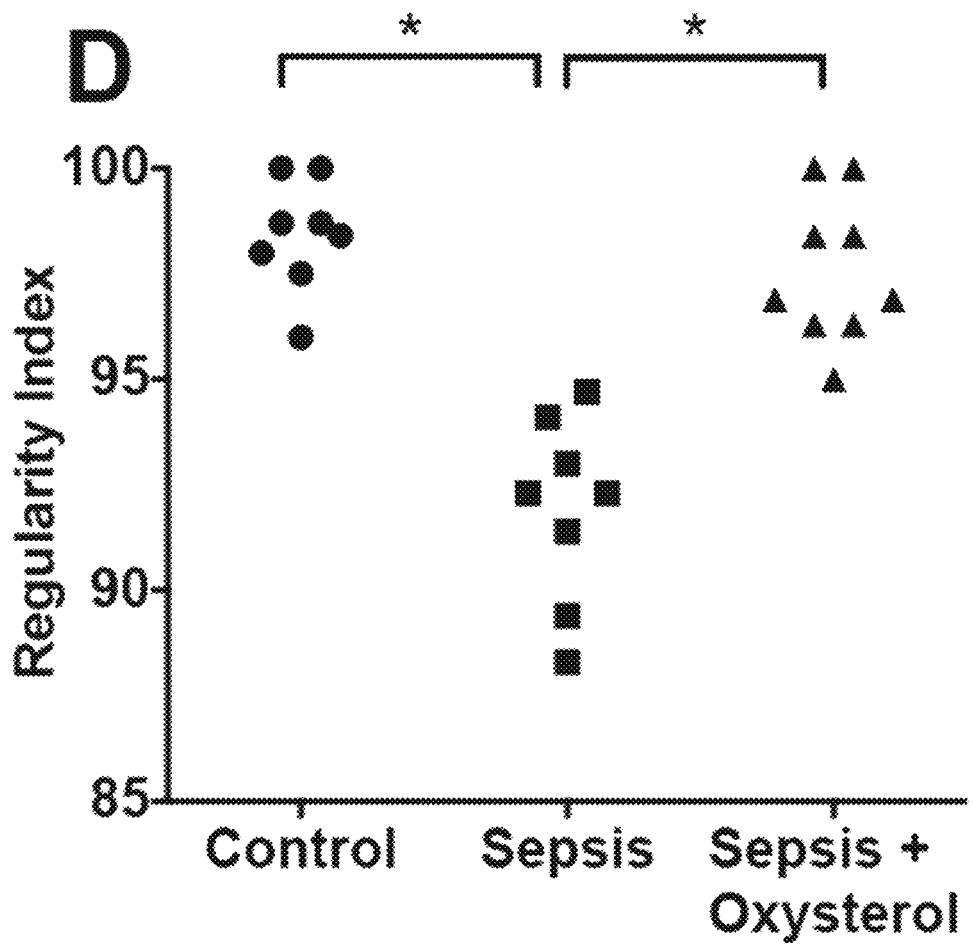
FIG. 4D is a graph illustrating the Regularity Index resulting from the gait measurements.

Regularity Index: Regularity Index is a measure of inter-paw coordination, and disturbances in regularity may be a result of cerebral injury. The Regularity Index was determined for uninjured control mice (FIG. 4A,D), sepsis mice (FIG. 4B,D), and septic mice treated with the oxysterol 20HC (FIG. 4 C,D). FIG. 4 shows decreased regularity index for untreated mature mice that survived perinatal sepsis when compared to uninjured age-matched littermates. Remarkably, sepsis injured littermates treated with the oxysterol (20HC) completely reversed any observed deficits in Regularity Index (FIG. 4D).

Figures 5A, 5B:
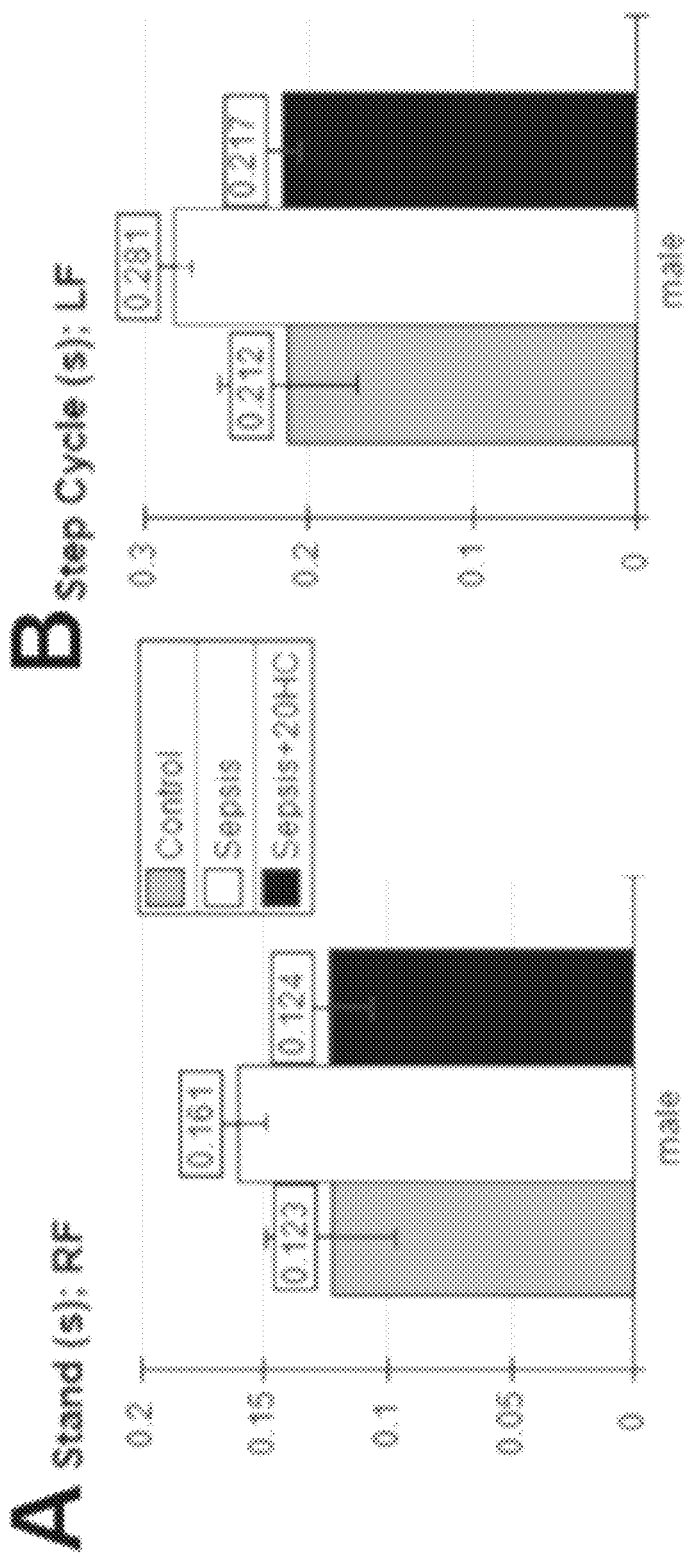

Stand and step cycle: Stand and step cycle are measures of the length of time the animal's paws are in contact with the platform as they walk. Increased stand and step cycle times are measures of gait instability. FIGS. 5A and 5B demonstrate that sepsis injured mice possessed an increased stand and step cycle, while those treated with the oxysterol resulted in similar values to the uninjured control mice.

Swing and swing speed: Swing and swing speed are measures of the animals "rocking" as they walk. While the swing was increased in perinatal sepsis survivors (FIG. 5C), the swing speed was decreased in sepsis survivors (FIG. 5D) consistant with an unsteady gait. Administration of 20α-hydroxycholesterol therapy reversed all of these measures of gait disturbances.

Example 5. Detection of Oxysterols in Human Breast Milk

Figure 6A:
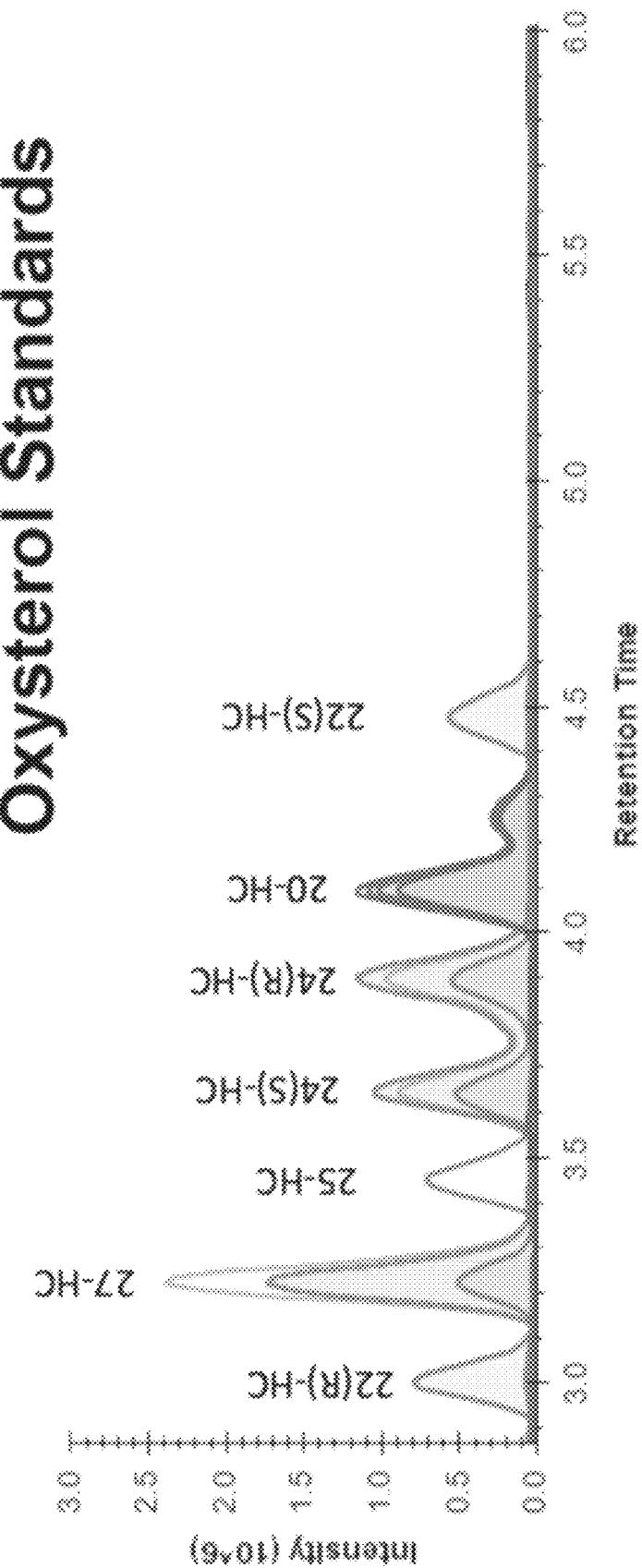
FIG. 6A is a graph showing results of mass spectrometry experiments to analyze oxysterol standards.
Figure 6B:
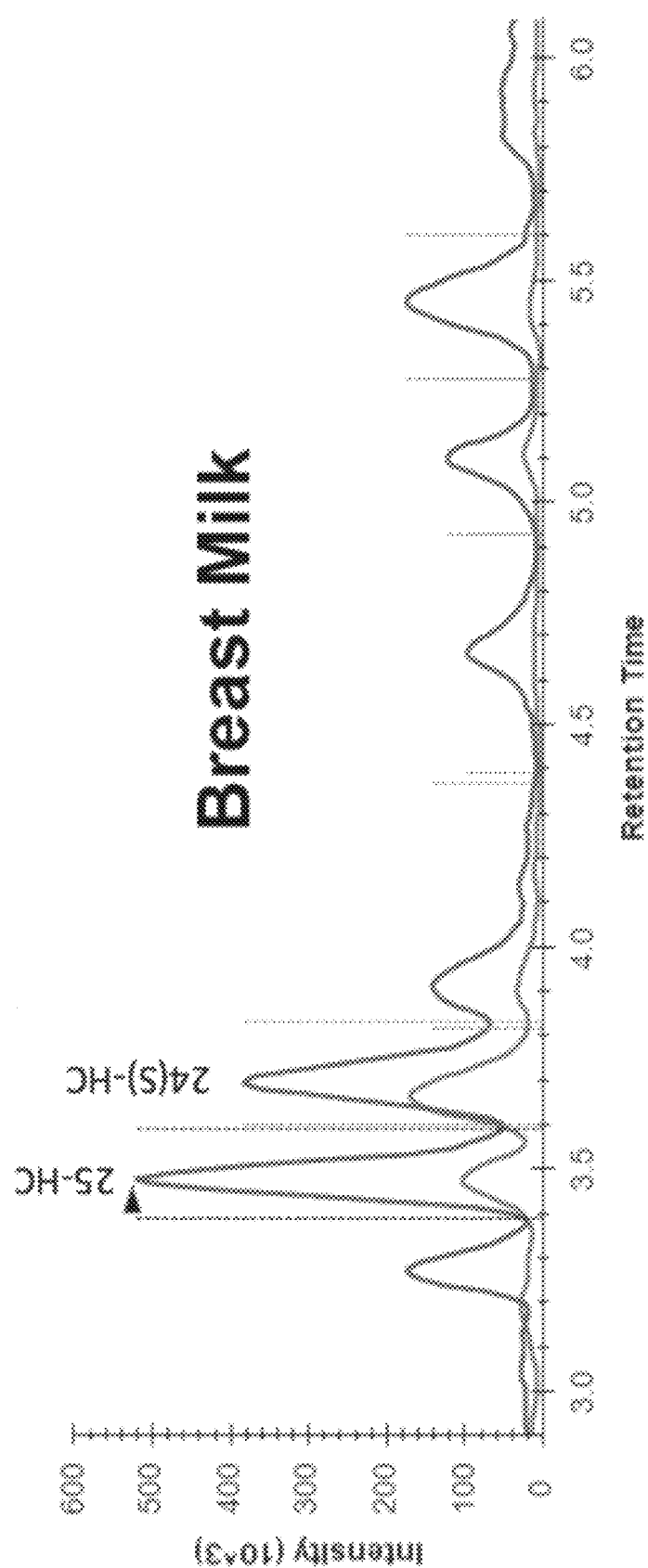
FIG. 6B is a graph depicting the measurement of different oxysterols in human breast milk.
Figure 7:
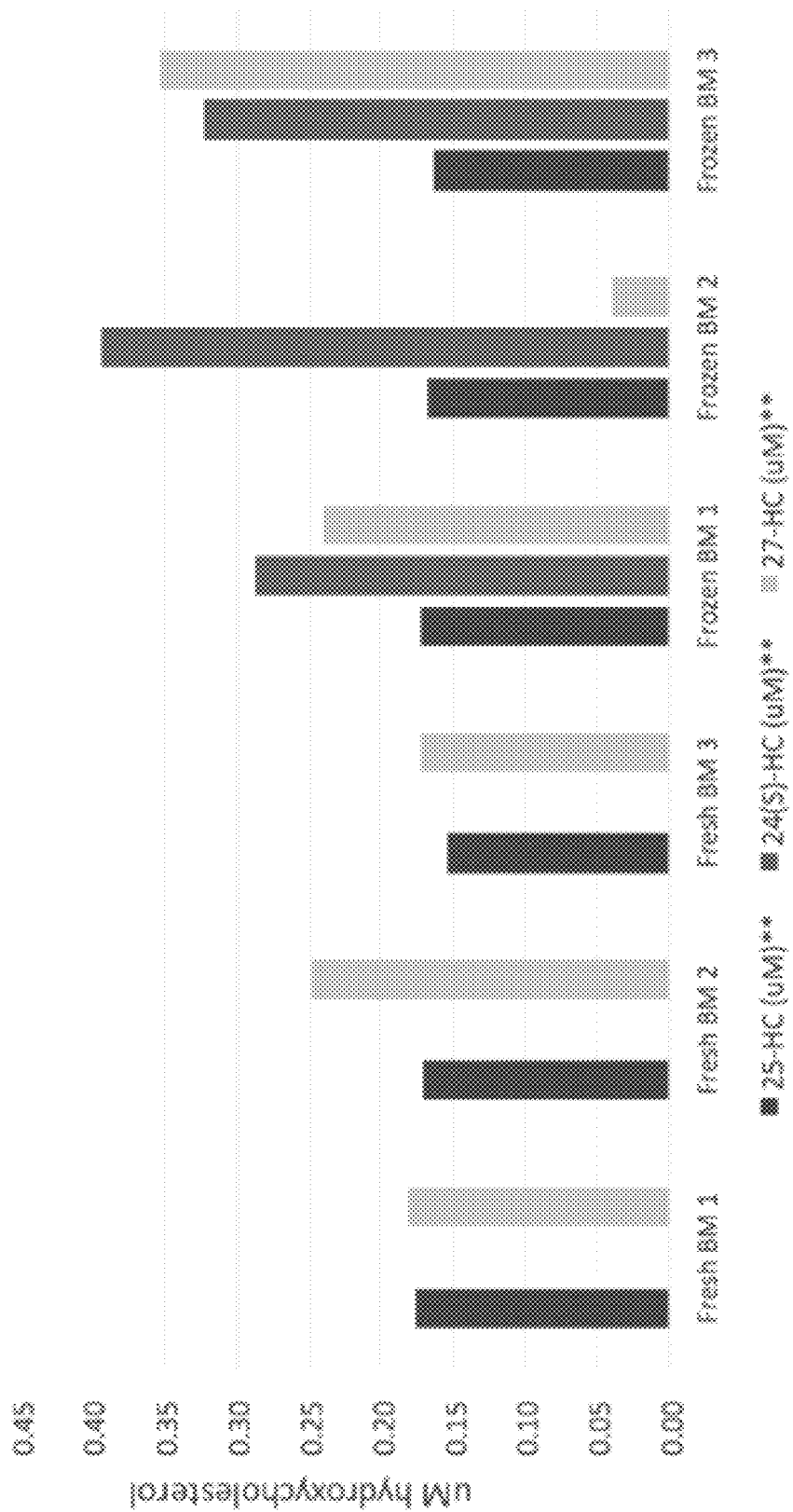
FIG. 7 is a graph depicting the measurement of different oxysterol concentrations in human breast milk.

Mass spectrometry assays were employed to identify oxysterols that are present in human breast milk. Samples of freshly pumped human breast milk were obtained. Half of each sample was immediately frozen on dry ice and stored at −80° C. The remainder was stored at 4° C. for six days before analysis. Breast milk samples were then analyzed by mass spectrometry and compared to oxysterols standards (FIG. 6A,B). While 20α-hydroxycholesterol was not detected in human breast milk, abundant levels of 24-hydroxycholesterol (24HC), 25-hydroxycholesterol (25HC), and 27-hydroxycholesterol (27HC) were observed (FIG. 7).

Figure 8:
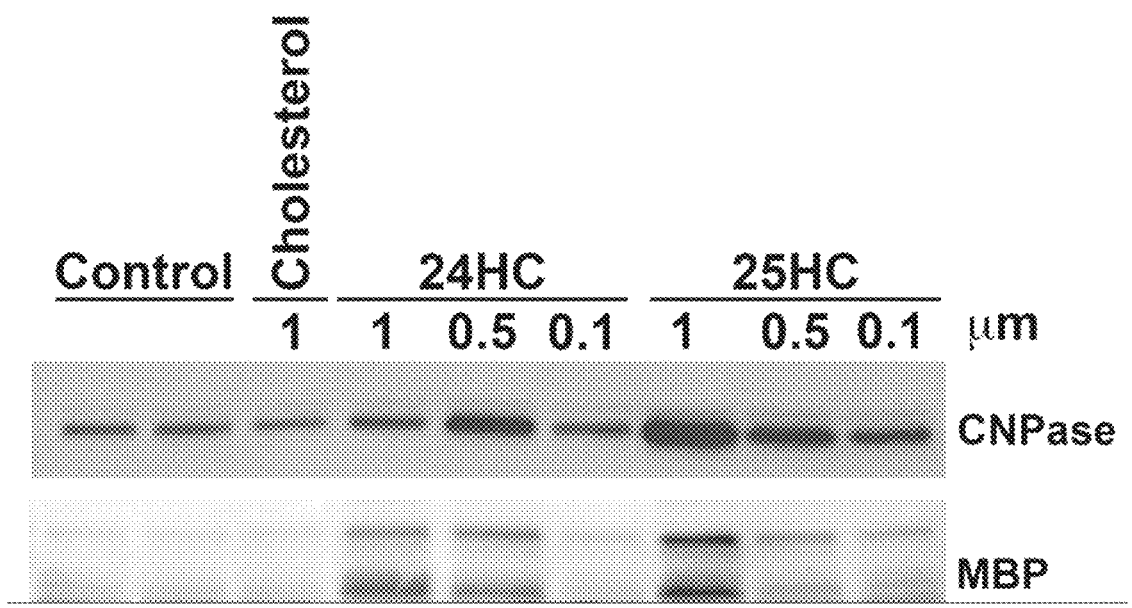
FIG. 8 is a western blot analysis. Stem cells were treated with oxysterols at doses indicated for 5 days then allowed to differentiate for 18 days. Protein lysates were probed for oligodendrocyte-associated proteins CNPase and myelin basic protein (MBP).

Example 6. In Vitro Oligodendrocyte Differentiation from Neural Stem Cells with Breast Milk-Associated 24-Hydroxycholesterol and 25-Hydroxycholesterol Primary neural stem cells were treated with 24-hydroxycholesterol and 25-hydroxycholesterol at 1 μm and 0.5 μm for five days, then allowed to differentiate for 18 days. Protein lysates were probed for oligodendrocyte-associated proteins CNPase and myelin basic protein (MBP). Exposure of neural stem cells to these oxysterols induced expression of oligodendrocyte-associated proteins CNPase and MBP, suggesting similar activity as 20α-hydroxycholesterol (FIG. 8).

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

For reasons of completeness, various aspects of the present disclosure are set out in the following numbered clauses:

Clause 1. A method of promoting oligodendrogenesis in a subject in need thereof, the method comprising administering a therapeutically effective amount of at least one oxysterol.

Clause 2. The method of clause 1, wherein the oxysterol promotes differentiation of neural stem cells into oligodendrocytes.

Clause 3. The method of clause 1 or clause 2, wherein the oxysterol comprises a cholesterol derivative oxidized at any of carbons 20-27.

Clause 4. The method of any one of clauses 1-3, wherein the oxysterol is selected from the group consisting of: 20α-hydroxycholesterol; 22(R)-hydroxycholesterol; 22(S)-hydroxycholesterol; 24(R)-hydroxycholesterol; 24(S)-hydroxycholesterol; 25-hydroxycholesterol; and 27-hydroxycholesterol; or a pharmaceutically acceptable salt thereof.

Clause 5. The method of clause 1, wherein the subject in need thereof suffers from a disease or disorder associated with myelin injury.

Clause 6. The method of clause 5, wherein the disease or disorder is selected from at least one of neonatal brain injury, traumatic brain injury, spinal cord injury, cerebral palsy, seizures, autism spectrum disorders, cognitive delay, multiple sclerosis, stroke, leukodystrophy, schizophrenia and bipolar disorder.

Clause 7. The method of clause 6, wherein the neonatal brain injury is selected from at least one of diffuse white matter injury, periventricular leukomalacia (PVL), hypoxic-ischemic encephalopathy (HIE), neonatal stroke, and grade 3-4 intraventricular hemorrhages (IVH).

Clause 8. The method of any one of clauses 1-7, wherein the oxysterol promotes myelination.

Clause 9. A method of repairing injured myelin in a subject in need thereof, the method comprising administering a therapeutically effect amount of an oxysterol.

Clause 10. The method of clause 9, wherein the injured myelin is a result of brain injury.

Clause 11. The method of clause 10, wherein the brain injury is traumatic brain injury or neonatal brain injury.

Clause 12. The method of clause 11, wherein the neonatal brain injury is selected from at least one of diffuse white matter injury, periventricular leukomalacia (PVL), hypoxic-ischemic encephalopathy (HIE), neonatal stroke, and grade 3-4 intraventricular hemorrhages (WH).

Clause 13. The method of any one of clauses 9-12, wherein the oxysterol promotes differentiation of neural stem cells into oligodendrocytes.

Clause 14. The method of any one of clauses 9-13, wherein the oxysterol comprises a cholesterol derivative oxidized at any of carbons 20-27.

Clause 15. The method of any one of clauses 9-14, wherein the oxysterol is selected from the group consisting of: 20α-hydroxycholesterol; 22(R)-hydroxycholesterol; 22(S)-hydroxycholesterol; 24(R)-hydroxycholesterol; 24(S)-hydroxycholesterol; 25-hydroxycholesterol; and 27-hydroxycholesterol; or a pharmaceutically acceptable salt thereof.

Clause 16. A pharmaceutical composition comprising at least one oxysterol and at least one pharmaceutically acceptable carrier.

Clause 17. The pharmaceutical composition of clause 16, further comprising human breast milk.

What is claimed is:

1. A method of promoting oligodendrogenesis in a subject in need thereof, the method comprising:
   administering to a subject a therapeutically effective amount of at least one oxysterol, wherein the subject has cerebral palsy.

2. The method of claim 1, wherein the at least one oxysterol promotes differentiation of neural stem cells into oligodendrocytes.

3. The method of claim 1, wherein the at least one oxysterol comprises a cholesterol derivative oxidized at any of carbons 20-27.

4. The method of claim 1, wherein the at least one oxysterol is selected from the group consisting of:
   20α-hydroxycholesterol;
   22(R)-hydroxycholesterol;
   22(S)-hydroxycholesterol;
   24(R)-hydroxycholesterol;
   24(S)-hydroxycholesterol;
   25-hydroxycholesterol; and
   27-hydroxycholesterol; or a pharmaceutically acceptable salt thereof.

5. The method of claim 1, wherein the at least one oxysterol promotes myelination.

6. The method of claim 1, wherein the at least one oxysterol is 20α-hydroxycholesterol, 24(R)-hydroxycholesterol, 24(S)-hydroxycholesterol, or a pharmaceutically acceptable salt thereof.

7. A method of repairing injured myelin in a subject in need thereof, the method comprising:
   administering to a subject a therapeutically effective amount of at least one oxysterol, wherein the injured myelin is a result of cerebral palsy.

8. The method of claim 7, wherein the at least one oxysterol promotes differentiation of neural stem cells into oligodendrocytes.

9. The method of claim 7, wherein the at least one oxysterol comprises a cholesterol derivative oxidized at any of carbons 20-27.

10. The method of claim 7, wherein the at least one oxysterol is selected from the group consisting of:
    20α-hydroxycholesterol;
    22(R)-hydroxycholesterol;
    22(S)-hydroxycholesterol;
    24(R)-hydroxycholesterol;
    24(S)-hydroxycholesterol;
    25-hydroxycholesterol; and
    27-hydroxycholesterol; or a pharmaceutically acceptable salt thereof.

11. The method of claim 7, wherein the at least one oxysterol is 20α-hydroxycholesterol, 24(R)-hydroxycholesterol, 24(S)-hydroxycholesterol, or a pharmaceutically acceptable salt thereof.

12. A pharmaceutical composition comprising human breast milk, at least one oxysterol, and at least one pharmaceutically acceptable carrier.

* * * * *